US012630627B2

(12) United States Patent
Liu et al.

(10) Patent No.: US 12,630,627 B2
(45) Date of Patent: May 19, 2026

(54) FORMULATION COMPRISING ANTI-PD-1/HER2 BISPECIFIC ANTIBODY, METHOD FOR PREPARING SAME AND USE THEREOF

(71) Applicants:INNOVENT BIOLOGICS (SUZHOU) CO., LTD., Suzhou (CN); BEIJING HANMI PHARMACEUTICAL CO., LTD., Beijing (CN)

(72) Inventors: Yanghan Liu, Suzhou (CN); Yidong Ma, Suzhou (CN); Yinjue Wang, Suzhou (CN); Kaisong Zhou, Suzhou (CN)

(73) Assignees: INNOVENT BIOLOGICS (SUZHOU) CO., LTD., Suzhou (CN); BEIJING HANMI PAHRMACEUTICAL CO., LTD., Beijing (CN)

( * ) Notice: Subject to any disclaimer, the term of this patent is extended or adjusted under 35 U.S.C. 154(b) by 1146 days.

(21) Appl. No.: 17/631,641

(22) PCT Filed: Aug. 6, 2020

(86) PCT No.: PCT/CN2020/107441
§ 371 (c)(1),
(2) Date: Jan. 31, 2022

(87) PCT Pub. No.: WO2021/023267
PCT Pub. Date: Feb. 11, 2021

(65) Prior Publication Data
US 2022/0281972 A1 Sep. 8, 2022

(30) Foreign Application Priority Data
Aug. 7, 2019 (CN) ......................... 201910726334.X

(51) Int. Cl.
| | |
|---|---|
| *C07K 16/28* | (2006.01) |
| *A61K 9/00* | (2006.01) |
| *A61K 39/00* | (2006.01) |
| *A61K 47/26* | (2006.01) |
| *A61P 35/00* | (2006.01) |

(52) U.S. Cl.
CPC ........ *C07K 16/2803* (2013.01); *A61K 9/0019* (2013.01); *A61K 47/26* (2013.01); *A61P 35/00* (2018.01); *A61K 2039/505* (2013.01)

(58) Field of Classification Search
None
See application file for complete search history.

(56) References Cited

U.S. PATENT DOCUMENTS

| | | | |
|---|---|---|---|
| 8,372,396 B2 | 2/2013 | Andya et al. | |
| 9,220,776 B2 | 12/2015 | Sharma et al. | |
| 11,319,378 B2 * | 5/2022 | Liu ........................ | C07K 16/32 |
| 11,753,471 B2 * | 9/2023 | Liu ........................ | C07K 16/32 |
| | | | 424/136.1 |
| 2017/0028063 A1 * | 2/2017 | Chandramouli ....... | A61K 47/10 |
| 2019/0367633 A1 | 12/2019 | Liu et al. | |

FOREIGN PATENT DOCUMENTS

| | | | | | |
|---|---|---|---|---|---|
| CA | 2830806 | A1 * | 10/2012 | .............. | A61P 31/00 |
| CN | 102961745 | A | 3/2013 | | |
| CN | 105168125 | A | 12/2015 | | |
| CN | 107198773 | A | 9/2017 | | |
| CN | 107955072 | A | 4/2018 | | |
| WO | 2004/091658 | A1 | 10/2004 | | |
| WO | 2010/102241 | A1 | 9/2010 | | |
| WO | 2011012637 | A2 | 2/2011 | | |
| WO | 2015/095412 | A1 | 6/2015 | | |
| WO | 2018/002339 | A1 | 1/2018 | | |
| WO | 2018/068336 | A2 | 4/2018 | | |
| WO | WO-2018068336 | A1 * | 4/2018 | .......... | A61K 39/395 |
| WO | WO-2018090950 | A1 * | 5/2018 | ............. | C07K 16/32 |
| WO | 2018/187057 | A1 | 10/2018 | | |
| WO | 2019/153200 | A1 | 8/2019 | | |

OTHER PUBLICATIONS

Urchiyama, BBA-Proteins&Proteomics, 2014, 1844, 2041-2052 (Year: 2014).*
Viola Margarida et al:"Subcutaneous delivery of monoclonal antibodies: How do we get there?", Journal of Controlled Release, vol. 286, 2018, pp. 301-314.
Neal Whitaker et al: "A Formulation Development Approach to Identify and Select stable Ultra High-Concentration Monoclonal Antibody Formulations With Reduced Viscosities", Journal of Pharmaceutical Sciences, vol. 106, No. 11, 2017, pp. 3230-3241.
Uchiyama Susumu Ed—Shugar David et al: "Liquid formulation for antibody drugs", Biochimica Et Biophysica Acta (BBA)—Proteins & Proteomics, vol. 1844, No. 11, 2014, pp. 2041-2052.
J Kang et al: "Rapid Formulation Development for Monoclonal Antibodies—Bioprocess International BioProcess International", Apr. 12, 2016, retrieved from: https://bioprocessintl.com/manufacturing/formulation/rapid-formulation-development-for-monoclonal-antibodies/.
Tugcu et al., Maximizing productivity of chromatography steps for purification of monoclonal antibodies, Biotechnology and Bioengineering, 99 (2008) 599-613.
Kelley et al., Weak partitioning chromatography for anion exchange purification of monoclonal antibodies, Biotechnology and Bioengineering, 101 (2008) 553-566.
Richard et al, Applications of CE SDS gel in development of biopharmaceutical antibody-based products, Electrophoresis, 2008, 29, 3612-3620.

(Continued)

*Primary Examiner* — Michael Szperka
*Assistant Examiner* — Samantha Lake Hopkins
(74) *Attorney, Agent, or Firm* — LEASON ELLIS LLP

(57) ABSTRACT

The present invention relates to formulations comprising an anti-PD-1/HER2 bispecific antibody, and in particular to a pharmaceutical formulation comprising the anti-PD-1/HER2 bispecific antibody, a buffer, a stabilizer and a surfactant. Furthermore, the present invention also relates to therapeutic or prophylactic use of these formulations.

7 Claims, 4 Drawing Sheets

Specification includes a Sequence Listing.

(56) References Cited

OTHER PUBLICATIONS

Shahrokh: "Approaches to Analysis of Aggregates and Demonstrating Mass Balance in Pharmaceutical Protein (Basic Fibroblast Growth Factor) Formulations": J. Pharm. Scien., 83:1645-1650 (1994).

Sluzky: "Chromatographic Methods for Quantitative Analysis of Native, Denatured, and Aggregated Basic Fibroblast Growth Factor in Solution Formulations": Pharm. Res., 11:485 (1994).

El Walily: "Simultaneous determination of tenoxicam and 2-aminopyridine using derivative spectrophotometry and high-performance liquid chromatography": J. Pharm. Bio. Anal., 15:1923-1928 (1997).

Usami: "The effect of pH, hydrogen peroxide and temperature on the stability of human monoclonal antibody": J. Pharm. Bio. Anal., 14:1133-1140 (1996).

R. Yang et al., High resolution separation of recombinant monoclonal antibodies by size exclusion ultra-high performance liquid chromatography (SE-UHPLC), Journal of Pharmaceutical and Biomedical Analysis (2015), http://dx.doi.org/10.1016/j.jpba.2015.02.032.

Goyon et al., Protocols for the analytical characterization of therapeutic monoclonal antibodies, I-Non-denaturing chromatographic techniques, Journal of Chromatography, 2017, http://dx.doi.org/10.1016/j.jchromb.2017.05.010.

Salas-Solano O et al, Robustness of iCIEF methodology for the analysis of monoclonal antibodies: an interlaboratory study, J Sep Sci. 2012; 35(22):3124-9.

Dada et al, Characterization of acidic and basic variants of IgG1 therapeutic monoclonal antibodies based on non-denaturing IEF fractionation, Electrophoresis. 2015; 36:2695-2702.

Daugherty, et al., Formulation and delivery issues for monoclonal antibody therapeutics. Advanced Drug Delivery Reviews, vol. 58, pp. 686-706 (2006).

Wang, et al., Antibody structure, instability, and formulation, Journal of Pharmaceutical Sciences, vol. 96, Issue 1, pp. 1-26 (2007).

International Search Report and Written Opinion of PCT/CN2020/107441, mailed on Nov. 11, 2020, with translations .

Manning M.C. et al.: "Stability of protein pharmaceuticals"; Pharm. Res., 1989, vol. 6, No. 11, pp. 903-918.

* cited by examiner

Structure of an anti-PD-1/HER2 bispecific antibody

Trend of change in turbidity of anti-PD-1/HER2 bispecific antibody formulations at pH 5.0–6.5 ($OD_{350\,nm}$ method)

Trend of change in protein purity of samples determined by SEC-HPLC (40±2 °C)

Trend of change in protein purity of samples determined by non-reduced CE-SDS (40±2 °C)

Trend of change in protein purity of samples determined by reduced CE-SDS (40±2 °C)

Trend of change in charge variant-principal component of samples determined by iCIEF (40±2 °C)

Anti-PD-1/HER2 bispecific antibody formulations comprising different stabilizers
Trend of change in charge variant-principal component over time determined by
iCIEF (40 °C)

Anti-PD-1/HER2 bispecific antibody formulations comprising different stabilizers
Trend of change in charge variant-principal component over time determined by
iCIEF (25±2 °C)

SEQUENCE LISTING

<160> NUMBER OF SEQ ID NOS: 14

<210> SEQ ID NO 1
<211> LENGTH: 321
<212> TYPE: DNA
<213> ORGANISM: Artificial Sequence
<220> FEATURE:
<223> OTHER INFORMATION: Light chain variable region of anti-human HER2
      antibody

<400> SEQUENCE: 1
gacattcaga tgactcagag cccttcttca ctgtcagctt ccgtgggcga cagagtcact        60
atcacctgcc gcgcaagtca ggatgtgaac accgcagtcg cctggtacca gcagaagcct       120
ggcaaagctc caaagctgct gatctacagc gcatctttcc tgtattctgg agtgcccagt       180
aggtttagtg ggtcacggtc cggtaccgac ttcacactga ctatctccag cctgcagcct       240
gaggattttg ccacatacta ttgccagcag cactatacca cacccctac tttcggccag        300 ggaaccaaag tggagatcaa g                                                  321

<210> SEQ ID NO 2
<211> LENGTH: 107
<212> TYPE: PRT
<213> ORGANISM: Artificial Sequence
<220> FEATURE:
<223> OTHER INFORMATION: Light chain variable region of anti-human HER2
      antibody

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 3
<211> LENGTH: 321
<212> TYPE: DNA
<213> ORGANISM: Artificial Sequence
<220> FEATURE:
<223> OTHER INFORMATION: Light chain constant region of anti-human HER2
      antibody

<400> SEQUENCE: 3
cgaactgtgg ccgctccaag cgtcttcatt tttccaccct ctgacgaaca gctgaagtca        60
gggacagctt ccgtggtctg tctgctgaac aattttttacc ccaggggaggc caaagtgcag     120 tggaaggtcg ataacgctct gcagagcgga aattctcagg agagtgtgac agaacaggac       180
tcaaaagatt ccacttatag cctgtctagt accctgacac tgtccaaggc agactacgaa       240
aagcataaag tgtatgcctg tgaggtcaca catcagggtc tgtcaagccc cgtcactaag       300
tccttcaatc gtggcgaatg c                                                  321

-continued

<210> SEQ ID NO 4
<211> LENGTH: 107
<212> TYPE: PRT
<213> ORGANISM: Artificial Sequence
<220> FEATURE:
<223> OTHER INFORMATION: Light chain constant region of anti-human HER2
      antibody

<400> SEQUENCE: 4

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 5
<211> LENGTH: 360
<212> TYPE: DNA
<213> ORGANISM: Artificial Sequence
<220> FEATURE:
<223> OTHER INFORMATION: Heavy chain variable region of anti-human HER2
      antibody

<400> SEQUENCE: 5
gaggtgcagc tggtcgaaag tggggggtgggg ctggtgcagc caggcggatc actgaggctg      60
tcctgcgccg ctagcggctt caacatcaaa gacacctata ttcactgggt ccgacaggca     120
ccagggaagg gtctggaatg ggtggctcgt atctacccta caaatggtta cactagatat     180
gccgactccg tgaaaggccg gtttactatt tctgctgata ccagtaagaa cacagcatac     240
ctgcagatga atagcctgag ggctgaggat accgcagtgt actattgctc tcggtggggg     300
ggtgacggct tctacgctat ggattattgg ggccagggaa ctctggtcac cgtgtccagc     360

<210> SEQ ID NO 6
<211> LENGTH: 120
<212> TYPE: PRT
<213> ORGANISM: Artificial Sequence
<220> FEATURE:
<223> OTHER INFORMATION: Heavy chain variable region of anti-human HER2
      antibody

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

-continued

```
Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
                100                 105                 110

Gly Thr Leu Val Thr Val Ser Ser
        115                 120

<210> SEQ ID NO 7
<211> LENGTH: 990
<212> TYPE: DNA
<213> ORGANISM: Artificial Sequence
<220> FEATURE:
<223> OTHER INFORMATION: Heavy chain constant region of anti-human HER2
      antibody

<400> SEQUENCE: 7
gcttcaacaa aaggaccttc cgtgtttcca ctggcaccct ctagtaagag tacttcagga      60
ggaaccgcag cactgggatg tctggtgaag gactacttcc cagagcccgt caccgtgtct     120
tggaacagtg gagcactgac ctccggggtc catacatttc tgccgtgct gcagtcatcc      180 ggtctgtata gcctgagctc tgtggtcaca gtcccaagtt catccctggg cacccagaca     240
tacatctgca cgtgaatca caaaccttcc aatactaagg tcgacaagaa agtggaacca      300
aaaagctgtg ataagactca tacctgccca ccttgtcctg caccagagct gctgggaggt     360
ccaagcgtgt tcctgtttcc acccaagccc aaagacacac tgatgatttc tcgcacaccc     420
gaagtcactt gtgtggtcgt ggacgtgtcc cacgaggatc ctgaagtcaa gttcaactgg     480
tacgtggatg gcgtcgaggt gcataatgct aagaccaaac ccagagagga acagtacaac     540
agcacctatc gcgtcgtgtc tgtcctgaca gtgctgcacc aggattggct gaacggaaag     600
gagtacaagt gcaaagtgag caacaaggcc ctgcccgctc ctatcgagaa gaccatttct     660
aaggctaaag gccagcctag agaaccacag gtgtatacag agcctccaag tcgcgacgag     720
ctgacaaaaa accaggtctc cctgacttgt ctggtgaagg gattctaccc tagcgatatc     780
gcagtggagt gggaatctaa tgggcagcca gaaaacaatt ataagaccac cccCctgtg     840 ctggactcag atggttcctt ctttctgctg agtgtgctga ccgtggacaa gtccaggtgg     900
cagcagggga acgtcttttc ctgcagcgtg atgcatgagg ccctgcacaa tcattacaca     960
cagaaatctc tgagtctgtc accaggaaag                                       990

<210> SEQ ID NO 8
<211> LENGTH: 330
<212> TYPE: PRT
<213> ORGANISM: Artificial Sequence
<220> FEATURE:
<223> OTHER INFORMATION: Heavy chain constant region of anti-human HER2
      antibody

<400> SEQUENCE: 8

Ala Ser Thr Lys Gly Pro Ser Val Phe Pro Leu Ala Pro Ser Ser Lys
1                   5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Glu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Leu Ser Val Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 9
<211> LENGTH: 321
<212> TYPE: DNA
<213> ORGANISM: Artificial Sequence
<220> FEATURE:
<223> OTHER INFORMATION: Light chain variable region of anti-human PD-1
      antibody

<400> SEQUENCE: 9
gacatccaga tgacccagtc ccctagcagc gtgagcgctt ccgtgggcga cagggtgacc        60
atcacctgca gggcctccca gggcatctcc tcctggctgg cctggtatca acagaagccc       120
ggcaaggccc ccaagctgct gatctccgct gcctcctccc tgcagtccgg agtgccttcc       180
aggttcagcg gttctggctc cggcaccgac ttcaccctga ccatctcctc cctgcagccc       240
gaggacttcg ccacctacta ctgccagcag gccaaccacc tgcctttcac cttcggcggc       300
ggcaccaagg tggagatcaa g                                                 321

<210> SEQ ID NO 10
<211> LENGTH: 107
<212> TYPE: PRT
```

-continued

---

<213> ORGANISM: Artificial Sequence
<220> FEATURE:
<223> OTHER INFORMATION: Light chain variable region of anti-human PD-1
      antibody

<400> SEQUENCE: 10

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Ser Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn His Leu Pro Phe
                85                  90                  95

Thr Phe Gly Gly Gly Thr Lys Val Glu Ile Lys
            100                 105

<210> SEQ ID NO 11
<211> LENGTH: 360
<212> TYPE: DNA
<213> ORGANISM: Artificial Sequence
<220> FEATURE:
<223> OTHER INFORMATION: Heavy chain variable region of anti-human PD-1
      antibody

<400> SEQUENCE: 11
caggtgcagc tggtgcagtc cggagccgag gtgaagaagc ccggctcctc cgtgaaggtg     60
tcctgcaagg cctccggcgg caccttctcc tccaccgcca tctcctgggt gaggcaggct    120
cctggccagg gactggagtg gatgggaggc atctggccct ccttcggcac agcctcctac    180
gcccagaagt tccagggcag ggtgaccatc accgccgacg agagcacctc caccgcctac    240
atggagctga gctccctgag gtccgaggac accgccgtgt actactgtgc cagggccgag    300
tactcctcca ccggcatctt cgactactgg ggccagggca ccctggtgac agtgtcctcc    360

<210> SEQ ID NO 12
<211> LENGTH: 120
<212> TYPE: PRT
<213> ORGANISM: Artificial Sequence
<220> FEATURE:
<223> OTHER INFORMATION: Heavy chain variable region of anti-human PD-1
      antibody

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Thr
            20                  25                  30

Ala Ile Ser Trp Val Arg Gln Ala Pro Gly Gln Gly Leu Glu Trp Met
        35                  40                  45

Gly Gly Ile Trp Pro Ser Phe Gly Thr Ala Ser Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

-continued

Ala Arg Ala Glu Tyr Ser Ser Thr Gly Ile Phe Asp Tyr Trp Gly Gln
            100                 105                 110

Gly Thr Leu Val Thr Val Ser Ser
        115                 120

<210> SEQ ID NO 13
<211> LENGTH: 990
<212> TYPE: DNA
<213> ORGANISM: Artificial Sequence
<220> FEATURE:
<223> OTHER INFORMATION: Heavy chain constant region of anti-human PD-1
      antibody

<400> SEQUENCE: 13
gcttcaacaa aaggaccttc cgtgtttcca ctggcaccct ctagtaagag tacttcagga      60
ggaaccgcag cactgggatg tctggtgaag gactacttcc cagagcccgt caccgtgtct     120
tggaacagtg gagcactgac ctccggggtc catacatttc ctgccgtgct gcagtcatcc     180
ggtctgtata gcctgagctc tgtggtcaca gtcccaagtt catccctggg cacccagaca     240
tacatctgca acgtgaatca caaaccttcc aatactaagg tcgacaagaa agtggaacca     300
aaaagctgtg ataagactca tacctgccca ccttgtcctg caccagagct gctgggaggt     360
ccaagcgtgt tcctgtttcc acccaagccc aaagacacac tgatgatttc tcgcacaccc     420
gaagtcactt gtgtggtcgt ggacgtgtcc cacgaggatc ctgaagtcaa gttcaactgg     480
tacgtggatg gcgtcgaggt gcataatgct aagaccaaac ccagagagga acagtacaac     540
agcacctatc gcgtcgtgtc tgtcctgaca gtgctgcacc aggattggct gaacggaaag     600
gagtacaagt gcaaagtgag caacaaggcc ctgcccgctc ctatcgagaa gaccatttct     660
aaggctaaag gccagcctag agaaccacag gtgtatacac tgcctccaag tcgcgacgag     720
ctgacaaaaa accaggtctc cctgctgtgt ctggtgaagg gattctaccc tagcgatatc     780
gcagtggagt gggaatctaa tgggcagcca gaaaacaatt ataagaccac accccctgtg     840
ctgcggtcag atggttcctt ctttctgtac agtaaactga ccgtggacaa gtccaggtgg     900
cagcagggga cgtctttttc ctgcagcgtg atgcatgagg ccctgcacaa tcattacaca     960
cagaaatctc tgagtctgtc accaggaaag                                      990

<210> SEQ ID NO 14
<211> LENGTH: 330
<212> TYPE: PRT
<213> ORGANISM: Artificial Sequence
<220> FEATURE:
<223> OTHER INFORMATION: Heavy chain constant region of anti-human PD-1
      antibody

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys

-continued

```
                 85                    90                    95

Lys Val Glu Pro Lys Ser Cys Asp Lys Thr His Thr Cys Pro Pro Cys
            100               105               110

Pro Ala Pro Glu Leu Leu Gly Gly Pro Ser Val Phe Leu Phe Pro Pro
        115               120               125

Lys Pro Lys Asp Thr Leu Met Ile Ser Arg Thr Pro Glu Val Thr Cys
    130               135               140

Val Val Val Asp Val Ser His Glu Asp Pro Glu Val Lys Phe Asn Trp
145               150               155               160

Tyr Val Asp Gly Val Glu Val His Asn Ala Lys Thr Lys Pro Arg Glu
            165               170               175

Glu Gln Tyr Asn Ser Thr Tyr Arg Val Val Ser Val Leu Thr Val Leu
            180               185               190

His Gln Asp Trp Leu Asn Gly Lys Glu Tyr Lys Cys Lys Val Ser Asn
            195               200               205

Lys Ala Leu Pro Ala Pro Ile Glu Lys Thr Ile Ser Lys Ala Lys Gly
    210               215               220

Gln Pro Arg Glu Pro Gln Val Tyr Thr Leu Pro Pro Ser Arg Asp Glu
225               230               235               240

Leu Thr Lys Asn Gln Val Ser Leu Leu Cys Leu Val Lys Gly Phe Tyr
            245               250               255

Pro Ser Asp Ile Ala Val Glu Trp Glu Ser Asn Gly Gln Pro Glu Asn
            260               265               270

Asn Tyr Lys Thr Thr Pro Pro Val Leu Arg Ser Asp Gly Ser Phe Phe
            275               280               285

Leu Tyr Ser Lys Leu Thr Val Asp Lys Ser Arg Trp Gln Gln Gly Asn
    290               295               300

Val Phe Ser Cys Ser Val Met His Glu Ala Leu His Asn His Tyr Thr
305               310               315               320

Gln Lys Ser Leu Ser Leu Ser Pro Gly Lys
            325               330
```

FORMULATION COMPRISING ANTI-PD-1/HER2 BISPECIFIC ANTIBODY, METHOD FOR PREPARING SAME AND USE THEREOF

TECHNICAL FIELD

The present invention relates to the field of antibody formulations. More specifically, the present invention relates to a pharmaceutical formulation, in particular to a stable liquid formulation, comprising a recombinant anti-programmed death receptor 1 (PD-1) and anti-human epidermal growth factor receptor 2 (HER2) bispecific antibody (also known as an anti-PD-1/HER2 bispecific antibody), a method for preparing the pharmaceutical formulation, and therapeutic and/or prophylactic use of the pharmaceutical formulation.

BACKGROUND

Overexpression of human epidermal growth factor receptor 2 (HER2) (also known as NEU, ERBB-2, CD340 or p185) is associated with a variety of cancers, including breast cancer, ovarian cancer, gastric cancer, uterine cancer, melanoma and cholangiocarcinoma. For example, HER2 overexpression is observed in invasive and metastatic breast cancer and in breast cancer with a high rate of recurrence and/or poor patient prognosis.

One approach for treating HER2-overexpressing cancers is to use anti-HER2 antibodies that inhibit HER2 signaling. For example, trastuzumab is a therapeutic anti-HER2 antibody that blocks intracellular signaling mediated by HER2, and is widely used to treat HER2-overexpressing tumors. Unfortunately, their anti-tumor effect in clinical applications is often not as good as that in preclinical experiments. In the prior art, anti-HER2 antibodies are commonly administered in combination with chemotherapeutic drugs and the like (Slamon D J et al., *N Engl J Med*, 344:783-792, 2001).

In recent years, with the study of immune checkpoint molecules, it has been found that activation of inhibitory signaling pathways of immune checkpoints results in the inability of T lymphocytes to effectively exert a killing effect on tumors (Yao S, Zhu Y and Chen L, Advances in targeting cell surface signaling molecules for immune modulation, *Nat Rev Drug Discov*, 2013, 12(2):130-146), which results in, from one aspect, poor anti-tumor effect of drugs that target only target points on tumor cells (e.g., trastuzumab).

Programmed death protein-1 (PD-1) is an important immune checkpoint protein and is a 55 kDa type I transmembrane protein. It is mainly expressed inducibly on the surface of activated T cells, and is also expressed on cells such as B cells, NK cells, monocytes and DC cells. It has been identified that two cell surface glycoprotein ligands for PD-1 are programmed death protein ligand 1 (PD-L1) and programmed death protein ligand 2 (PD-L2). The ligands for PD-1 are highly expressed on many cancer cells. Binding of PD-1 to a ligand for PD-1 results in T cell apoptosis, immunologic unresponsiveness, T cell "depletion" and secretion of IL-10, etc., and thus, blocking the PD1 pathway can restore T cell function in cancer patients (Sheridan, *Nature Biotechnology*, 30(2012), 729-730). Monoclonal antibodies against PD-1 have been developed, for example, nivolumab of Bristol-Myers Squibb (BMS) and pembrolizumab of Merck. Nivolumab (trade name OPDIVO®) is a fully humanized IgG4 antibody molecule, and pembrolizumab (trade name KEYTRUDA®) is a humanized IgG4 antibody molecule. The anti-PD-1 monoclonal antibodies, upon binding to PD-1 on T lymphocytes, can inhibit the binding of PD-1 to its ligands PD-L1 and PD-L2, thereby promoting the activation and proliferation of T lymphocytes and the production of immune-activating cytokines such as IL-2, and relieving the inhibition of the immune monitoring of the T lymphocytes with anti-tumor activity by PD-1.

In view of the importance of the immune checkpoint molecule PD-1 in the modulation of immune responses, the inventors carried out research with keen determination and have obtained an anti-PD-1/HER2 bispecific antibody targeting both PD-1 and HER2, which is capable of simultaneously targeting HER2 on tumor cells and activating T lymphocytes, and thus shows the advantage of reducing side effects while enhancing anti-tumor effect. The patent application number of the anti-PD-1/HER2 bispecific antibody is PCT/CN2018/075851 (filed on Feb. 8, 2018), wherein an anti-PD-1/HER2 bispecific antibody consisting of an anti-PD-1 half antibody and an anti-HER2 half antibody is constructed and expressed. The anti-PD-1/HER2 bispecific antibody was administered to tumor-bearing mice produced by inoculating immunodeficient NCG mice with HCC1954 human breast cancer cells, and the results show that compared with an anti-HER2 monoclonal antibody or an anti-PD-1 monoclonal antibody, the anti-PD-1/HER2 bispecific antibody has significantly improved anti-tumor activity and can remarkably reduce the tumor volume.

There is a need in the art for anti-PD-1/HER2 bispecific antibody formulations that can be used to treat, prevent or delay a variety of diseases associated with the HER2 signaling pathway and the PD-1 signaling pathway, and the formulations have good stability; when the anti-PD-1/HER2 bispecific antibody is formulated in a liquid, the anti-PD-1/HER2 bispecific antibody in the liquid solution is not prone to decomposition, aggregation or undesirable chemical modification.

BRIEF SUMMARY

The present invention satisfies the above-described need by providing a pharmaceutical formulation comprising an anti-PD-1/HER2 bispecific antibody protein specifically binding to PD-1 and HER2. The antibody formulation disclosed herein can allow the antibody to be formulated in a manner that is suitable for administration to a subject and can allow the antibody to maintain its stability in storage and subsequent use as well.

In one aspect, the present invention provides a liquid antibody formulation comprising (i) an anti-PD-1/HER2 bispecific antibody protein; (ii) a buffer; (iii) a stabilizer; and (iv) a surfactant.

The anti-PD-1/HER2 bispecific antibody protein in the antibody formulation disclosed herein comprises a first half antibody and a second half antibody, wherein the first half antibody comprises a first VH/VL unit specifically binding to PD-1, and the second half antibody comprises a second VH/VL unit specifically binding to HER2. In some embodiments, the anti-PD-1/HER2 bispecific antibody protein is capable of binding to PD-1 on the surface of T lymphocytes with an affinity constant of at least about $10^7$ $M^{-1}$, preferably about $10^8$ $M^{-1}$ and more preferably about $10^9$ $M^{-1}$ or greater, thereby blocking the binding of PD-1 to its ligands, promoting activation and proliferation of T lymphocytes and production of immune-activating cytokines such as IL-2; and capable of binding to HER2 on the surface of tumor cells with an affinity constant of at least about $10^7$ $M^{-1}$, preferably about $10^8$ $M^{-1}$ and more preferably about $10^9$ M$^{-1}$ or greater, thereby blocking intracellular signaling mediated by HER2 and exerting an anti-tumor effect.

In one embodiment, the anti-PD-1/HER2 bispecific antibody protein is a recombinant anti-PD-1/HER2 bispecific antibody protein disclosed in PCT application No. PCT/CN2018/075851 (filed on Feb. 8, 2018), the content of which is incorporated herein by reference in its entirety for the purpose of the present application. In one embodiment, the anti-PD-1/HER2 bispecific antibody protein comprises a first half antibody and a second half antibody, wherein the first half antibody comprises a first VH/VL unit specifically binding to PD-1, and the second half antibody comprises a second VH/VL unit specifically binding to HER2, wherein the first VH/VL unit comprises all heavy chain CDRs and light chain CDRs contained in paired heavy chain variable region/light chain variable region sequences set forth in SEQ ID NO: 12/SEQ ID NO: 10, and the second VH/VL unit comprises all heavy chain CDRs and light chain CDRs contained in paired heavy chain variable region/light chain variable region sequences set forth in SEQ ID NO: 6/SEQ ID NO: 2.

In one embodiment, the anti-PD-1/HER2 bispecific antibody protein comprises a first half antibody and a second half antibody, wherein the first half antibody comprises a first VH/VL unit specifically binding to PD-1, and the second half antibody comprises a second VH/VL unit specifically binding to HER2, wherein the first VH/VL unit comprises paired heavy chain variable region/light chain variable region sequences set forth in SEQ ID NO: 12/SEQ ID NO: 10 or sequences having at least 90%, 91%, 92%, 93%, 94%, 95%, 96%, 97%, 98%, 99% or higher sequence identity to the paired heavy chain variable region/light chain variable region sequences, and the second VH/VL unit comprises paired heavy chain variable region/light chain variable region sequences set forth in SEQ ID NO: 6/SEQ ID NO: 2 or sequences having at least 90%, 91%, 92%, 93%, 94%, 95%, 96%, 97%, 98%, 99% or higher sequence identity to the paired heavy chain variable region/light chain variable region sequences.

In one embodiment, the anti-PD-1/HER2 bispecific antibody protein comprises a first half antibody and a second half antibody, wherein the first half antibody comprises heavy chain sequences set forth in SEQ ID NO: 12 and SEQ ID NO: 14 or heavy chain sequences having at least 90%, 95%, 98% or 99% identity thereto in N to C direction and comprises light chain sequences set forth in SEQ ID NO: 10 and SEQ ID NO: 4 or light chain sequences having at least 90%, 95%, 98% or 99% identity thereto in N to C direction, and the second half antibody comprises heavy chain sequences set forth in SEQ ID NO: 6 and SEQ ID NO: 8 or heavy chain sequences having at least 90%, 95%, 98% or 99% identity thereto in N to C direction and comprises light chain sequences set forth in SEQ ID NO: 2 and SEQ ID NO: 4 or light chain sequences having at least 90%, 95%, 98% or 99% as identity thereto in N to C direction.

In one embodiment, the anti-PD-1/HER2 bispecific antibody protein is an anti-PD-1/HER2 bispecific antibody protein recombinantly expressed in HEK293 cells or HEK293T, HEK293F or HEK293E cells obtained by modification based on HEK293 cells, and in CHO cells or CHO-S, CHO-dhfr⁻, CHO/DG44 or ExpiCHO cells obtained by modification based on CHO cells.

In one embodiment, a concentration of the anti-PD-1/HER2 bispecific antibody protein in the liquid antibody formulation disclosed herein is about 1-150 mg/mL. In another embodiment, a concentration of the anti-PD-1/HER2 bispecific antibody protein in the liquid antibody formulation disclosed herein is about 10-100 mg/mL. In other embodiments, a concentration of the anti-PD-1/HER2 bispecific antibody protein in the liquid antibody formulation disclosed herein is about 10, 20, 30, 40, 50, 60, 70, 80, 90 or 100 mg/mL.

In one embodiment, a concentration of the buffer in the liquid antibody formulation disclosed herein is about 5-50 mM. In one embodiment, a concentration of the buffer in the liquid antibody formulation disclosed herein is about 10-30 mM, e.g., about 10, 15, 20, 25 or 30 mM.

In one embodiment, the buffer is selected from histidine, histidine hydrochloride and a combination thereof.

In one embodiment, a concentration of the stabilizer in the liquid antibody formulation disclosed herein is about 50-500 mM. In one embodiment, a concentration of the stabilizer in the liquid antibody formulation disclosed herein is about 100-400 mM, e.g., about 100, 150, 200, 250, 300, 350 or 400 mM.

In one embodiment, the stabilizer is selected from polyol (e.g., sorbitol), saccharide (e.g., sucrose or trehalose) and any combination thereof.

In yet another embodiment, the stabilizer is selected from combinations of polyol (e.g., sorbitol), saccharide (e.g., sucrose or trehalose) and any combination thereof with an antioxidant. In one embodiment, a total concentration of the stabilizer in the liquid antibody formulation is about 50-500 mM, preferably about 100-400 mM, e.g., about 100, 150, 200, 250, 300, 350 or 400 mM, wherein a concentration of the antioxidant is about 1-50 mM, preferably about 5-40 mM, e.g., about 5, 10, 20, 30 or 40 mM. In one embodiment, the antioxidant is methionine.

In one embodiment, a concentration of the surfactant in the liquid antibody formulation disclosed herein is about 0.1-1 mg/mL. In one embodiment, a concentration of the surfactant in the liquid antibody formulation disclosed herein is about 0.2-0.8 mg/mL, e.g., about 0.2, 0.3, 0.4, 0.5, 0.6, 0.7 or 0.8 mg/mL.

In one embodiment, the surfactant is a nonionic surfactant. In one embodiment, the surfactant is selected from polysorbate surfactants. In one specific embodiment, the surfactant in the liquid antibody formulation disclosed herein is polysorbate 80.

In one embodiment, a pH of the liquid formulation is about 5.0-6.5. In some embodiments, a pH of the liquid formulation is any of about 5.0-6.5, e.g., about 5.0, 5.2, 5.4, 5.6, 5.8, 6.0, 6.2 or 6.4.

In one embodiment, the liquid formulation is a pharmaceutical formulation, preferably an injection, and more preferably a subcutaneous injection or an intravenous injection. In one embodiment, the liquid formulation is an intravenous infusion.

In one embodiment, the liquid antibody formulation disclosed herein comprises:

(i) about 1-150 mg/mL anti-PD-1/HER2 bispecific antibody protein;

(ii) about 5-50 mM histidine and/or histidine hydrochloride;

(iii) about 50-500 mM sorbitol, sucrose, trehalose and any combination thereof, or a combination of sorbitol, sucrose, trehalose and any combination thereof with methionine at a total concentration of about 50-500 mM, wherein a concentration of methionine is about 1-50 mM; and (iv) about 0.1-1 mg/mL polysorbate 80; wherein a pH of the liquid formulation is about 5.0-6.5, preferably about 5.5.

In one preferred embodiment, the liquid antibody formulation disclosed herein comprises:

(i) about 10-100 mg/mL anti-PD-1/HER2 bispecific antibody protein;

(ii) about 10-30 mM histidine and/or histidine hydrochloride;

(iii) about 100-400 mM sorbitol, sucrose and/or trehalose, or a combination of sorbitol, sucrose and/or trehalose with methionine at a total concentration of about 100-400 mM, wherein a concentration of methionine is about 5-40 mM; and (iv) about 0.2-0.8 mg/mL polysorbate 80; wherein a pH of the liquid formulation is about 5.0-6.5, preferably about 5.5.

In one preferred embodiment, the liquid antibody formulation disclosed herein comprises:

(i) about 20 mg/mL anti-PD-1/HER2 bispecific antibody protein;

(ii) about 10 mM histidine;

(iii) about 50 mg/mL sorbitol; and (iv) about 0.3 mg/mL polysorbate 80; wherein a pH of the liquid formulation is about 5.0-6.5, preferably about 5.5.

In one preferred embodiment, the liquid antibody formulation disclosed herein comprises:

(i) about 50 mg/mL anti-PD-1/HER2 bispecific antibody protein;

(ii) about 20 mM histidine;

(iii) about 50 mg/mL sorbitol; and (iv) about 0.2 mg/mL polysorbate 80; wherein a pH of the liquid formulation is about 5.0-6.5, preferably about 5.5.

In one preferred embodiment, the liquid antibody formulation disclosed herein comprises:

(i) about 50 mg/mL anti-PD-1/HER2 bispecific antibody protein;

(ii) about 20 mM histidine;

(iii) about 80 mg/mL sucrose; and (iv) about 0.2 mg/mL polysorbate 80; wherein a pH of the liquid formulation is about 5.0-6.5, preferably about 5.5.

In one preferred embodiment, the liquid antibody formulation disclosed herein comprises:

(i) about 50 mg/mL anti-PD-1/HER2 bispecific antibody protein;

(ii) about 20 mM histidine;

(iii) about 80 mg/mL trehalose; and (iv) about 0.2 mg/mL polysorbate 80; wherein a pH of the liquid formulation is about 5.0-6.5, preferably about 5.5.

In one preferred embodiment, the liquid antibody formulation disclosed herein comprises:

(i) about 50 mg/mL anti-PD-1/HER2 bispecific antibody protein;

(ii) about 20 mM histidine;

(iii) about 80 mg/mL sucrose and about 1.49 mg/mL methionine; and (iv) about 0.2 mg/mL polysorbate 80; wherein a pH of the liquid formulation is about 5.0-6.5, preferably about 5.5.

In one preferred embodiment, the liquid antibody formulation disclosed herein comprises:

(i) about 42 mg/mL anti-PD-1/HER2 bispecific antibody protein;

(ii) about 0.85 mg/mL histidine and about 3.17 mg/mL histidine hydrochloride;

(iii) about 80 mg/mL sucrose; and (iv) about 0.2 mg/mL polysorbate 80; wherein a pH of the liquid formulation is about 5.0-6.5, preferably about 5.5.

In another aspect, the present invention provides a solid antibody formulation obtained by solidifying the liquid antibody formulation disclosed herein. The solidification treatment is implemented by, e.g., crystallization, spray drying, or freeze drying. In one preferred embodiment, the solid antibody formulation is, e.g., in the form of lyophilized powder for injection. The solid antibody formulation can be reconstituted in a suitable vehicle prior to use to give a reconstituted formulation of the present invention. The reconstituted formulation is also a liquid antibody formulation disclosed herein. In one embodiment, the suitable vehicle is selected from water for injection, organic solvents for injection (including but not limited to, oil for injection, ethanol, propylene glycol, and the like), and combinations thereof.

The liquid formulation disclosed herein can be stably stored for a long period of time, e.g., at least 24 months or longer. In one embodiment, the liquid formulation disclosed herein can be stable after storage at about −80° C. to about 45° C., e.g., −80° C., about −30° C., about −20° C., about 0° C., about 5° C., about 25° C., about 35° C., about 38° C., about 40° C., about 42° C. or about 45° C., for at least 10 days, at least 20 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, at least 36 months, or longer.

In one embodiment, the liquid formulation disclosed herein can be stably stored for at least 24 months. In another embodiment, the liquid formulation disclosed herein is stable at a temperature of at least 40° C. In yet another embodiment, the liquid formulation disclosed herein remains stable at about 2-8° C. for at least 3 months, preferably at least 12 months, and more preferably at least 24 months. In one embodiment, the liquid formulation disclosed herein remains stable at room temperature or, e.g., about 25° C., for at least 2 months, preferably at least 3 months, and more as preferably at least 6 months. In yet another embodiment, the liquid formulation disclosed herein remains stable at about 40° C. for at least 2 weeks, preferably at least 1 month.

In one embodiment, the stability of the formulation can be indicated after storage by detecting changes in the appearance, visible particles, protein content, turbidity, purity and/or charge variants of the formulation. In one embodiment, the stability of the liquid formulation disclosed herein can be detected in a forced high temperature stress test, e.g., after storage at 40±2° C. for at least 1 week, 2 weeks or preferably 1 month, or in an accelerated test, e.g., after storage at 25±2° C. for at least 1 month or 2 months, or in a long-term test, e.g., after storage at 5±3° C. for at least 2 months or 3 months.

In one embodiment, the stability of the liquid formulation disclosed herein is visually inspected after storage, wherein the liquid formulation disclosed herein remains a clear to slightly opalescent, colorless to pale yellow liquid free of particles in appearance. In one embodiment, no visible particles exist in the formulation upon visual inspection under a clarity detector. In one embodiment, the stability of the liquid formulation disclosed herein is tested after storage by determining the change in protein content, wherein the change rate in protein content is no more than 20%, preferably no more than 10%, e.g., 7-8%, and more preferably no more than 5%, relative to an initial value on day 0 of storage, as measured, for example, by the ultraviolet spectrophotometry (UV) method. In one embodiment, the stability of the liquid formulation disclosed herein is tested after storage by determining the change in turbidity of the liquid formulation disclosed herein, wherein the change is no more than 0.06, preferably no more than 0.05, and more preferably no more than 0.04, relative to an initial value on day 0 of storage, as measured, for example, by the $OD_{350\ mm}$ method. In one embodiment, the stability of the liquid formulation disclosed herein is tested after storage by determining the change in purity of the liquid formulation disclosed herein, wherein the change in monomer purity is no more than 10%, e.g., no more than 5%, 4% or 3%, e.g., 1-2%, preferably no more than 1%, relative to an initial value on day 0 of storage, as measured by size exclusion-high performance liquid chromatography (SEC-HPLC). In one embodiment, the stability of the liquid formulation disclosed herein is tested after storage by determining the change in purity of the formulation disclosed herein, wherein the change in monomer purity is reduced by no more than 10%, e.g., no more than 5%, 4% or 3%, as measured by non-reduced and/or reduced capillary electrophoresis-sodium dodecyl sulfate (CE-SDS). In one embodiment, the stability of the liquid formulation disclosed herein is tested after storage by imaged capillary isoelectric focusing (iCIEF), wherein the total change in charge variants (principal component, acidic component and basic component) of the antibody is no more than 50%, e.g., no more than 40%, 30%, 20%, 10% or 5%, relative to an initial value on day 0 of storage. In one embodiment, the stability of the liquid formulation disclosed herein is tested after storage by cation exchange high performance liquid chromatography (CEX-HPLC), wherein the total change in the charge variants (principal component, acidic component and basic component) of the antibody is no more than 40%, e.g., no more than 38%, 36%, 34%, 32% or 30%, relative to an initial value on day 0 of storage.

In one embodiment, the formulation is stable after storage, e.g., at 2-8° C. for at least 24 months, at room temperature for at least 3 months, or at 40±2° C. for 1 month, and preferably, has one or more of the following characteristics:

(i) a purity greater than 90%, preferably greater than 95%, 96%, 97%, 98% or 99%, as measured by SEC-HPLC;

(ii) a purity greater than 90%, preferably greater than 92%, 94%, 96% or 98%, as measured by reduced or non-reduced CE-SDS;

(iii) total change ≤50% in components (principal component, acidic component and basic component) of the anti-PD-1/HER2 bispecific antibody protein in the formulation, e.g., ≤40%, 30%, 20%, 10% or 5%, relative to an initial value on day 0 of storage, as measured by iCIEF; and (iv) relative binding activity of the anti-PD-1/HER2 bispecific antibody protein in the formulation of 70-130%, e.g., 70%, 80%, 90%, 100%, 110%, 120% or 130%, relative to an initial value on day 0 of storage, as measured by ELISA.

In one aspect, the present invention provides a delivery device comprising the liquid antibody formulation or the solid antibody formulation disclosed herein. In one embodiment, the delivery device disclosed herein is provided in the form of a pre-filled syringe comprising the liquid antibody formulation or the solid antibody formulation disclosed herein, e.g., for use in intravenous, subcutaneous, intradermal or intramuscular injection, or intravenous infusion.

In another aspect, the present invention provides a method for delivering an anti-PD-1/HER2 bispecific antibody protein to a subject, e.g., a mammal, which comprises administering the liquid antibody formulation or the solid antibody formulation disclosed herein to the subject, the delivery being implemented, e.g., using a delivery device in the form of a pre-filled syringe.

In another aspect, the present invention provides use of the liquid antibody formulation or solid antibody formulation disclosed herein in preparing a delivery device (e.g., a pre-filled syringe) or medicament for treating, preventing or delaying a disorder associated with HER2 and PD-1 signaling pathways in a subject, wherein the disorder includes, e.g., various blood diseases and solid tumors, including but not limited to leukemia, lymphoma, myeloma, brain tumor, head and neck squamous cell carcinoma, non-small cell lung cancer, nasopharyngeal cancer, esophageal cancer, gastric cancer, pancreatic cancer, gall bladder cancer, cholangiocarcinoma, liver cancer, colorectal cancer, breast cancer, ovarian cancer, cervical cancer, endometrial cancer, uterine sarcoma, prostatic cancer, bladder cancer, renal cell carcinoma and melanoma.

Other embodiments of the present invention will become apparent by reference to the detailed description hereinafter.

BRIEF DESCRIPTION OF THE DRAWINGS

The preferred embodiments of the present invention described in detail below will be better understood when read in conjunction with the following drawings. For the purpose of illustrating the present invention, currently preferred embodiments are shown in the drawings. However, it should be understood that the present invention is not limited to accurate arrangement and means of the embodiments shown in the drawings.

DETAILED DESCRIPTION

Figure 1:
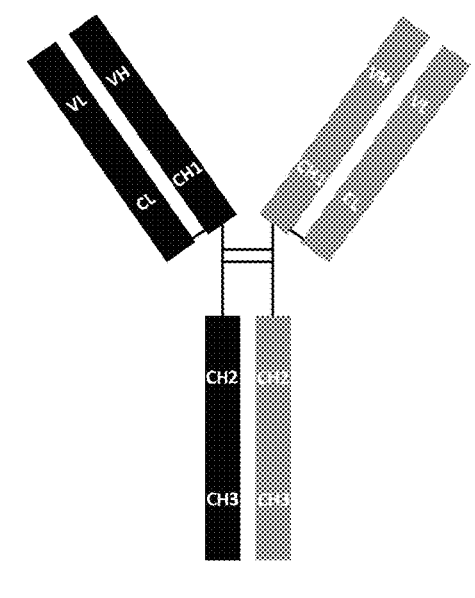
FIG. 1 illustrates the structure of an anti-PD-1/HER2 bispecific antibody comprising an anti-PD-1 half antibody molecule and an anti-HER2 half antibody molecule.

Before the present invention is described in detail, it should be understood that the present invention is not limited to the particular methods or experimental conditions described herein since the methods and conditions may vary. Further, the terms used herein are for the purpose of describing particular embodiments only and are not intended to be limiting.

Definitions

Unless defined otherwise, all technical and scientific terms used herein have the same meaning as commonly understood by those of ordinary skill in the art. For the purposes of the present invention, the following terms are defined below.

The term "about" used in combination with a numerical value is intended to encompass the numerical values in a range from a lower limit less than the specified numerical value by 5% to an upper limit greater than the specified numerical value by 5%.

The term "and/or", when used to connect two or more options, should be understood to refer to any one of the options or any two or more of the options.

As used herein, the term "comprise" or "comprising" is intended to include the described elements, integers or steps, but not to exclude any other elements, integers or steps. As used herein, the term "comprise" or "comprising", unless indicated otherwise, also encompasses the situation where the entirety consists of the described elements, integers or steps. For example, when referring to an antibody variable region "comprising" a particular sequence, it is also intended to encompass an antibody variable region consisting of the particular sequence.

As used herein, the term "antibody" is used in the broadest sense, and it refers to a protein comprising an antigen-binding site and encompasses natural and artificial antibodies with various structures, including but not limited to intact antibodies and antigen-binding fragments of antibodies.

The terms "whole antibody", "full-length antibody", "complete antibody" and "intact antibody" are used interchangeably herein to refer to a glycoprotein comprising at least two heavy chains (H) and two light chains (L) interconnected by disulfide bonds. Each heavy chain consists of a heavy chain variable region (abbreviated herein as VH) and a heavy chain constant region. Each heavy chain constant region consists of 3 domains CH1, CH2 and CH3. Each light chain consists of a light chain variable region (abbreviated herein as VL) and a light chain constant region. Each light chain constant region consists of one domain CL. The VH region and the VL region can be further divided into hypervariable regions (complementarity determining regions, or CDRs), with relatively conservative regions (framework regions, or FRs) inserted therebetween. Each VH or VL consists of three CDRs and four FRs, arranged from amino-terminus to carboxyl-terminus in the following order: FR1, CDR1, FR2, CDR2, FR3, CDR3 and FR4. The constant regions are not directly involved in binding of antibodies to antigens, but exhibit a variety of effector functions.

The term "humanized" antibody refers to a chimeric antibody comprising amino acid residues from non-human HVRs and amino acid residues from human FRs. In some embodiments, in a humanized antibody, all or substantially all HVRs (such as CDRs) correspond to those HVRs of a non-human antibody, and all or substantially all FRs correspond to those FRs of a human antibody. The humanized antibody may optionally comprise at least a portion of an antibody constant region derived from a human antibody. "Humanized forms" of antibodies (e.g., non-human antibodies) refer to antibodies that have been humanized.

The term "half antibody" or "hemimer" refers to a monovalent antigen-binding polypeptide. In some embodiments, the half antibody or hemimer comprises a VH/VL unit and optionally at least a portion of an immunoglobulin constant domain. In some embodiments, the half antibody or hemimer comprises one immunoglobulin heavy chain associated with one immunoglobulin light chain, or an antigen-binding fragment thereof. In some embodiments, the half antibody or hemimer is monospecific; that is, it binds to a single antigen or epitope. In some specific embodiments, the half antibody binds to HER2 and does not bind to PD-1. In some specific embodiments, the half antibody binds to PD-1 and does not bind to HER2. Those skilled in the art will readily appreciate that a half antibody may have an antigen-binding domain consisting of a single variable domain, e.g., derived from camelidae.

The term "VH/VL unit" refers to an antigen-binding region of an antibody comprising at least one VH CDR and at least one VL CDR. In some embodiments, the VH/VL unit comprises at least one, at least two or all three VH CDRs and at least one, at least two or all three VL CDRs. In certain embodiments, the VH/VL unit further comprises at least a portion of a framework region (FR). In some embodiments, the VH/VL unit comprises three VH CDRs and three VL CDRs. In some embodiments, the VH/VL unit comprises at least one, at least two, at least three or all four VH FRs and at least one, at least two, at least three or all four VL FRs.

As used herein, the term "bispecific antibody" comprises antigen-binding domains that specifically bind to epitopes on two different biomolecules. Unless otherwise stated, the order of antigens bound to the bispecific antibody in the listed name of the bispecific antibody is arbitrary. That is, in some embodiments, the terms "anti-PD-1/HER2 bispecific antibody" and "anti-HER2/PD-1 bispecific antibody" are used interchangeably. In some embodiments, the bispecific antibody comprises two half antibodies, wherein each half antibody comprises a single heavy chain variable region and optionally at least a portion of a heavy chain constant region, and comprises a single light chain variable region and optionally at least a portion of a light chain constant region. In some embodiments, the bispecific antibody comprises two half antibodies, wherein each half antibody comprises a single heavy chain variable region and a single light chain variable region but does not comprise more than one single heavy chain variable region and does not comprise more than one single light chain variable region. In some embodiments, the bispecific antibody comprises two half antibodies, wherein each half antibody comprises a single heavy chain variable region and a single light chain variable region, and wherein a first half antibody binds to a first antigen but does not bind to a second antigen, and a second half antibody binds to the second antigen but does not bind to the first antigen.

The term "antibody formulation" refers to a preparation in a form that allows the biological activity of an antibody as an active ingredient to be exerted effectively, and does not contain other components having unacceptable toxicity to a subject to which the formulation is to be administered. Such antibody formulations are generally sterile. Generally, the antibody formulation comprises a pharmaceutically acceptable excipient. A "pharmaceutically acceptable" excipient is an agent that can be reasonably administered to a mammal subject so that an effective dose of the active ingredient used in the formulation can be delivered to the subject. A concentration of the excipient is adapted to the mode of administration and may, for example, be acceptable for injection.

The term "anti-PD-1/HER2 bispecific antibody formulation", herein also referred to as the "antibody formulation disclosed herein", refers to a preparation comprising an anti-PD-1/HER2 bispecific antibody protein as an active ingredient and a pharmaceutically acceptable excipient. The anti-PD-1/HER2 bispecific antibody protein, as the active ingredient, is suitable for therapeutic or prophylactic administration to a human or non-human animal after the anti-PD-1/HER2 bispecific antibody protein is combined with the pharmaceutically acceptable excipient. The antibody formulation disclosed herein can be prepared, for example, as an aqueous liquid formulation, e.g., in a ready-to-use pre-filled syringe, or as a lyophilized formulation to be reconstituted (i.e., redissolved) by dissolution and/or suspension in a physiologically acceptable solution immediately prior to use. In some embodiments, the anti-PD-1/HER2 bispecific antibody protein formulation is in the form of a liquid formulation.

A "stable" antibody formulation is a formulation where the antibody retains an acceptable degree of physical and/or chemical stability after storage under specific conditions. Although the antibody in the antibody formulation may not maintain 100% of its chemical structure after storage for a specific period of time, the antibody formulation is considered "stable" when the antibody typically maintains about 90%, about 95%, about 96%, about 97%, about 98%, or about 99% of its structure or function after storage for a specific period of time. In some specific embodiments, the antibody aggregation or degradation or chemical modification is barely detected in the anti-PD-1/HER2 bispecific antibody protein formulation disclosed herein during manufacture, formulation, transportation and long-term storage, resulting in little or even no loss of biological activity of the anti-PD-1/HER2 bispecific antibody protein and exhibiting high stability. In some embodiments, the anti-PD-1/HER2 bispecific antibody protein formulation disclosed herein substantially retains its physical and chemical stability after storage. Preferably, the liquid formulation disclosed herein can remain stable at room temperature or at 40° C. for at least 2 weeks, and/or at 25° C. for at least 2 months, and/or at 2-8° C. for at least 24 months.

A variety of analytical techniques are known in the art for determining the stability of proteins, see, e.g., *Peptide and Protein Drug Delivery,* 247-301, Vincent Lee Ed., Marcel Dekker, Inc., New York, N.Y., Pubs (1991) and Jones, A. *Adv. Drug Delivery Rev.* 10: 29-90 (1993). Stability can be determined at a selected temperature and for a selected storage time. For example, the storage time can be selected based on the expected shelf life of the formulation. Alternatively, an accelerated stability test can be adopted. In some embodiments, the stability test is performed by conducting various stress tests on the antibody formulation. These tests can represent extreme conditions that a formulated antibody formulation may encounter during manufacture, storage or transportation, and can also represent conditions that may accelerate the instability of the antibody in the antibody formulation during non-manufacture, storage or transportation. For example, the formulated anti-PD-1/HER2 bispecific antibody protein formulation can be filled into a glass vial to test the stability of the antibody under high temperature stress.

The antibody can be considered to "maintain its physical stability" in the formulation if the formulation does not exhibit aggregation, precipitation, turbidity and/or denaturation, or exhibits very little aggregation, precipitation, turbidity, and/or denaturation after storage for a period of time. Safety issues arise as the aggregation of antibodies in the formulation can potentially lead to an increased immune response in a patient. Accordingly, there is a need to minimize or prevent the aggregation of antibodies in the formulation. Light scattering methods can be used to determine visible aggregates in the formulation. SEC can be used to determine soluble aggregates in the formulation. In addition, the stability of the formulation can be indicated by visually inspecting the appearance, color and/or clarity of the formulation, or by detecting the turbidity of the formulation by the $OD_{350\ nm}$ method, or by determining the purity of the formulation by non-reduced CE-SDS. In one embodiment, the stability of the formulation is measured by determining the percentage of antibody monomer in the formulation after storage at a particular temperature for a particular period of time, wherein the higher the percentage of antibody monomer in the formulation, the higher the stability of the formulation.

An "acceptable degree" of physical stability can represent that at least about 92% of anti-PD-1/HER2 bispecific antibody protein monomer is detected in the formulation after storage at a specific temperature for a specific period of time. In some embodiments, an acceptable degree of physical stability represents at least about 88%, 89%, 90%, 91%, 92%, 93%, 94%, 95%, 96%, 97%, 98% or 99% of anti-PD-1/HER2 bispecific antibody protein monomer after storage at a specific temperature for at least 2 weeks, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or longer. When the physical stability is assessed, the specific temperature at which the pharmaceutical formulation is stored can be any temperature from about −80° C. to about 45° C., e.g., about −80° C., about −30° C., about −20° C., about 0° C., about 4-8° C., about 5° C., about 25° C., about 35° C., about 37° C., about 40° C., about 42° C., or about 45° C. For example, a pharmaceutical formulation is considered stable if at least about 88%, 89%, 90%, 91%, 92%, 93%, 94%, 95%, 96%, 97%, 98% or 99% of anti-PD-1/HER2 bispecific antibody protein monomer is detected after storage at about 40±2° C. for 1 month or 4 weeks. A pharmaceutical formulation is considered stable if at least about 88%, 89%, 90%, 91%, 92%, 93%, 94%, 95%, 96%, 97%, 98% or 99% of anti-PD-1/HER2 bispecific antibody protein monomer is detected after storage at about 25° C. for 2 months. A pharmaceutical formulation is considered stable if at least about 88%, 89%, 90%, 91%, 92%, 93%, 94%, 95%, 96%, 97%, 98% or 99% of anti-PD-1/HER2 bispecific antibody protein monomer is detected after storage at about 5° C. for 9 months.

The antibody can be considered to "maintain its chemical stability" in the formulation if the antibody in the formulation does not exhibit significant chemical changes after storage for a period of time. Most of the chemical instability results from the formation of covalently modified forms of the antibody (e.g., charge variants of the antibody). Basic variants can be formed, for example, by aspartic acid isomerization, and N- and C-terminal modifications; acidic variants can be produced by deamidation, sialylation and glycation. Chemical stability can be assessed by detecting and/or quantifying chemically altered forms of the antibody. For example, charge variants of the antibody in the formulation can be detected by cation exchange chromatography (CEX) or imaged capillary isoelectric focusing (iCIEF). In one embodiment, the stability of the formulation is measured by determining the percentage change in charge variants of the antibody in the formulation after storage at a specific temperature for a specific period of time, wherein the smaller the change, the higher the stability of the formulation.

An "acceptable degree" of chemical stability can represent the percentage change in charge variants (e.g., principal component, acidic component or basic component) in the formulation of no more than 50%, e.g., no more than 30% or 20%, after storage at a specific temperature for a specific period of time. In some embodiments, an acceptable degree of chemical stability can represent the percentage change in charge variant-principal component of no more than about 50%, 40%, 30%, 20% or 15% after storage at a specific temperature for at least 2 weeks, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or longer. When the chemical stability is assessed, the temperature at which the pharmaceutical formulation is stored can be any temperature from about −80° C. to about 45° C., e.g., about −80° C., about −30° C., about −20° C., about 0° C., about 4-8° C., about 5° C., about 25° C., or about 45° C. For example, the pharmaceutical formulation can be considered stable if the percentage change in charge variant-principal component is less than about 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% after storage at 5° C. for 24 months. The pharmaceutical formulation can also be considered stable if the percentage change in charge variant-principal component is less than about 20%, 19%, 18%, 17%, 16%, 15%, 14%, 13%, 12%, 10%, 9%, 8%, 7%, 6%, 5%, 4%, 3%, 2%, 1%, 0.5% or 0.1% after storage at 25° C. for 2 months. The pharmaceutical formulation can also be considered stable if the percent change in charge variant-principal component is less than about 50%, 40%, 30%, 20%, 10%, 5% or 4% after storage at 40° C. for 1 month.

The term "lyophilized formulation" refers to a composition obtained or obtainable by a freeze-drying process of a liquid formulation. Preferably, it is a solid composition having a water content of less than 5%, preferably less than 3%.

The term "reconstituted formulation" refers to a liquid formulation obtained by dissolving and/or suspending a solid formulation (e.g., a lyophilized formulation) in a physiologically acceptable solution.

The term "room temperature" as used herein refers to a temperature of 15-30° C., preferably 20-27° C., and more preferably 25° C.

"Stress conditions" refer to environments that are chemically and/or physically unfavorable to antibody proteins and may result in unacceptable destabilization of the antibody proteins. "High temperature stress" refers to storing the antibody formulation at room temperature or higher (e.g., 40±2° C.) for a period of time. The stability of the antibody formulation can be tested by a high-temperature stress accelerated test.

As used herein, the term "parenteral administration" refers to administrations other than enteral and topical administrations, typically by injection or infusion, including but not limited to, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. In some embodiments, the stable anti-PD-1/HER2 bispecific antibody protein formulation disclosed herein is administered parenterally to a subject. In one embodiment, the anti-PD-1/HER2 bispecific antibody protein formulation disclosed herein is administered by subcutaneous, intradermal, intramuscular or intravenous injection to a subject.

I. Antibody Formulation

The present invention provides a stable liquid antibody formulation comprising (i) an anti-PD-1/HER2 bispecific antibody protein, (ii) a buffer, (iii) a stabilizer and (iv) a surfactant, wherein a pH of the antibody formulation is about 5.0-6.5. In one preferred embodiment, the liquid antibody formulation disclosed herein is in the form of an injection.

(i) Anti-PD-1/HER2 Bispecific Antibody Protein

The "anti-PD-1/HER2 bispecific antibody protein" in the antibody formulation disclosed herein comprises a first half antibody and a second half antibody, wherein the first half antibody comprises a first VH/VL unit specifically binding to PD-1, and the second half antibody comprises a second VH/VL unit specifically binding to HER2. In some embodiments, the anti-PD-1/HER2 bispecific antibody protein is capable of binding to PD-1 on the surface of T lymphocytes with an affinity constant of at least about $10^7$ $M^{-1}$, preferably about $10^8$ $M^{-1}$ and more preferably about $10^9$ $M^{-1}$ or greater, and is capable of binding to HER2 on the surface of tumor cells with an affinity constant of at least about $10^7$ $M^{-1}$, preferably about $10^8$ $M^{-1}$ and more preferably about $10^9$ $M^{-1}$ or greater, such that the antibody can be used as a therapeutic agent and/or a prophylactic agent featuring bispecific targeting of PD-1 molecules and HER2 molecules.

The VH/VL unit specifically binding to PD-1 or HER2 comprises 6 CDRs of a VH/VL unit derived from an anti-PD-1 antibody reported in any prior art and an anti-PD-1 antibody developed in the future, or sequences having one, two, three, four, five, six or more amino acid changes (e.g., amino acid substitutions or deletions) compared with one or more CDRs of the 6 CDRs; or comprises 6 CDRs of a VH/VL unit derived from an anti-HER2 antibody reported in any prior art and an anti-HER2 antibody developed in the future, or sequences having one, two, three, four, five, six or more amino acid changes (e.g., amino acid substitutions or deletions) compared with one or more CDRs of the 6 CDRs.

In one embodiment, the first VH/VL unit of the anti-PD-1/HER2 bispecific antibody protein that specifically binds to PD-1 comprises all 6 heavy and light chain CDRs contained in paired heavy chain variable region/light chain variable region sequences set forth in SEQ ID NO: 12/SEQ ID NO: 10 derived from the anti-PD-1 half antibody, or sequences having one, two, three, four, five, six or more amino acid changes (e.g., amino acid substitutions or deletions) compared with one or more CDRs of the 6 CDRs.

In one embodiment, the second VH/VL unit of the anti-PD-1/HER2 bispecific antibody protein that specifically binds to HER2 comprises all 6 heavy and light chain CDRs contained in paired heavy chain variable region/light chain variable region sequences set forth in SEQ ID NO: 6/SEQ ID NO: 2 derived from the anti-HER2 half antibody, or sequences having one, two, three, four, five, six or more amino acid changes (e.g., amino acid substitutions or deletions) compared with one or more CDRs of the 6 CDRs.

The term "CDR", "complementarity determining region" or "CDR region" (used interchangeably herein with a hyper-variable region "HVR") refers to an amino acid region in the variable region of an antibody that is primarily responsible for binding to an epitope of an antigen. The CDRs of the heavy and light chains are generally referred to as CDR1, CDR2, and CDR3, and are numbered sequentially from the N-terminus. Various schemes for determining the CDR sequence of a given VH, VL or VHH amino acid sequence are known in the art. For example, Kabat complementarity determining regions (CDRs) are determined based on sequence variability and are the most commonly used (Kabat et al., *Sequences of Proteins of Immunological Interest*, 5th Ed. Public Health Service, National Institutes of Health, Bethesda, Md. (1991)). Chothia scheme is based on the positions of structural loops (Chothia and Lesk, *J. mol. biol.* 196:901-917 (1987)). AbM HVRs are a compromise between Kabat HVRs and Chothia structural loops and are used by Oxford Molecular's AbM antibody modeling software. The "contact" HVRs are based on analysis of available complex crystal structures.

The amino acid changes, e.g., amino acid substitutions, are preferably conservative amino acid replacements. The "conservative amino acid replacement" refers to an amino acid alteration that results in the substitution of an amino acid with a chemically similar amino acid. Conservative substitution tables providing functionally similar amino acids are well known in the art. In any of the embodiments herein, in one preferred aspect, the conservatively substitution residue is from the conservative substitution Table A below, preferably the preferred substitution residues shown in Table A.

TABLE A

| Original residues | Exemplary replacement | Preferred conservative amino acid replacement |
|---|---|---|
| Ala (A) | Val; Leu; Ile | Val |
| Arg (R) | Lys; Gln; Asn | Lys |
| Asn (N) | Gln; His; Asp; Lys; Arg | Gln |

TABLE A-continued

| Original residues | Exemplary replacement | Preferred conservative amino acid replacement |
|---|---|---|
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Nle | Leu |
| Leu (L) | Nle; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Nle | Leu |

In one embodiment, the anti-PD-1/HER2 bispecific antibody protein comprises a first half antibody and a second half antibody, wherein the first half antibody comprises a first VH/VL unit specifically binding to PD-1, and the second half antibody comprises a second VH/VL unit specifically binding to HER2, wherein the first VH/VL unit comprises paired heavy chain variable region/light chain variable region sequences set forth in SEQ ID NO: 12/SEQ ID NO: 10 or sequences having at least 90%, 91%, 92%, 93%, 94%, 95%, 96%, 97%, 98%, 99% or higher sequence identity to the paired heavy chain variable region/light chain variable region sequences, and the second VH/VL unit comprises paired heavy chain variable region/light chain variable region sequences set forth in SEQ ID NO: 6/SEQ ID NO: 2 or sequences having at least 90%, 91%, 92%, 93%, 94%, 95%, 96%, 97%, 98%, 99% or higher sequence identity to the paired heavy chain variable region/light chain variable region sequences.

The type of the heavy chain constant regions of the first half antibody and the second half antibody in the anti-PD-1/HER2 bispecific antibody protein is not particularly limited, and is preferably the heavy chain constant region of an IgG1, IgG2 or IgG4 immunoglobulin or a sequence substantially identical (e.g., having at least 80%, 85%, 90%, 92%, 95%, 97%, 98%, 99% or higher identity) thereto. More preferably, the heavy chain constant region is a heavy chain constant region of a human IgG1 immunoglobulin, or a sequence substantially identical (for example, at least 80%, 85%, 90%, 92%, 95%, 97%, 98%, 99%, or higher identity) thereto.

In one embodiment, the anti-PD-1/HER2 bispecific antibody protein comprises a heavy chain constant region used in IgG1 (e.g., human IgG1). In yet another embodiment, the anti-PD-1/HER2 bispecific antibody protein comprises a heavy chain constant region of IgG4 (e.g., human IgG4). For example, Fc domains of the two heavy chains in the anti-PD-1/HER2 bispecific antibody each comprise a hinge region with "CPPC" amino acid residues, and/or the Fc domains comprise Y349C and S354C (according to the "EU numbering" of Kabat), respectively, and thus the anti-PD-1 half antibody and the anti-HER2 half antibody form interchain disulfide bonds in the Fc regions, thereby stabilizing correct pairing of the anti-PD-1 half antibody and the anti-HER2 half antibody.

In one embodiment, the anti-PD-1 half antibody and/or the anti-HER2 half antibody of the anti-PD-1/HER2 bispecific antibody protein comprise, in the Fc domain, amino acid mutations that affect an effector function of the antibody. In one specific embodiment, the effector function is antibody-dependent cell-mediated cytotoxicity (ADCC). In one embodiment, the amino acid mutations are present in the CH2 domain of the Fc region, e.g., the anti-PD-1/HER2 bispecific antibody protein comprises amino acid substitutions at positions 234 and 235 (EU numbering) of the Fc region of the anti-PD-1 half antibody and/or the anti-HER2 half antibody. In one specific embodiment, the amino acid substitutions are L234A and L235A (also referred to as "LALA mutations").

In yet another embodiment, the light chain of the anti-PD-1/HER2 bispecific antibody protein comprises a kappa light chain constant region or a lambda light chain constant region, for example, a human kappa light chain constant region or a human lambda light chain constant region.

In one embodiment, two heavy chains of the anti-PD-1/HER2 bispecific antibody protein comprise a protuberance ("knob") and a cavity ("hole") in their Fc domains, respectively, or vice versa, and the protuberance (or cavity) in the Fc domain of one heavy chain can be placed in the cavity (or protuberance) in the Fc domain of the other heavy chain, such that the two heavy chains form a stable "knob-in-hole" association with each other. In one embodiment, the amino acid substitution T366W is contained in one of the two heavy chains, and the amino acid substitutions T366S, L368A, and Y407V (EU numbering) are contained in the other heavy chain. Thus, the protuberance in one chain can be placed in the cavity in the other chain, which promotes the correct pairing of the two heavy chains of the anti-PD-1/HER2 bispecific antibody protein.

In one embodiment, the immunoglobulin CH1 domain and CL domain of the heavy chain and the light chain in each half antibody of the anti-PD-1/HER2 bispecific antibody protein comprise a protuberance and a cavity, respectively, or vice versa, and the protuberance (or cavity) in the CH1 domain can be placed in the cavity (or protuberance) in the CL domain, such that the heavy chain and the light chain in each half antibody also form a stable "knob-in-hole" association with each other.

In one embodiment, the anti-PD-1/HER2 bispecific antibody protein comprises a first half antibody and a second half antibody, wherein the first half antibody comprises heavy chain sequences set forth in SEQ ID NO: 12 and SEQ ID NO: 14 or heavy chain sequences having at least 90%, 95%, 98% or 99% identity thereto in N to C direction and comprises light chain sequences set forth in SEQ ID NO: 10 and SEQ ID NO: 4 or light chain sequences having at least 90%, 95%, 98% or 99% identity thereto in N to C direction, and the second half antibody comprises heavy chain sequences set forth in SEQ ID NO: 6 and SEQ ID NO: 8 or heavy chain sequences having at least 90%, 95%, 98% or 99% identity thereto in N to C direction and comprises light chain sequences set forth in SEQ ID NO: 2 and SEQ ID NO: 4 or light chain sequence having at least 90%, 95%, 98% or 99% identity thereto in N to C direction.

As used herein, the term "sequence identity" refers to the degree to which sequences are identical on a nucleotide-by-nucleotide or amino acid-by-amino acid basis in a comparison window. The "percent sequence identity" can be calculated by the following steps: comparing two optimally aligned sequences in a comparison window; determining a number of positions in which nucleic acid bases (e.g., A, T, C, G and I) or amino acid residues (e.g., Ala, Pro, Ser, Thr, Gly, Val, Leu, Ile, Phe, Tyr, Trp, Lys, Arg, His, Asp, Glu, Asn, Gln, Cys, and Met) are the same in the two sequences to give the number of matched positions; dividing the number of matched positions by the total number of positions in the comparison window (i.e., the window size); and multiplying the result by 100 to give a percent sequence identity. Optimal alignment for determining the percent sequence identity can be achieved in a variety of ways known in the art, for example, using publicly available computer software such as BLAST, BLAST-2, ALIGN, or Megalign (DNASTAR) software. Those skilled in the art can determine suitable parameters for alignment of the sequences, including any algorithms necessary to achieve optimal alignment in a full-length sequence range or target sequence region being compared.

The anti-PD-1/HER2 bispecific antibody protein in the antibody formulation disclosed herein is capable of simultaneously binding to PD-1 and HER2 proteins and maintains the affinity constant as of each parent antibody, so that the HER2 signaling pathway and the PD-1 signaling pathway can be blocked, and thus the antibody formulation can be used to treat, prevent or delay various diseases or disorders associated with the HER2 signaling pathway and/or the PD-1 signaling pathway.

In one preferred embodiment, the anti-PD-1/HER2 bispecific antibody protein disclosed herein is the recombinant anti-PD-1/HER2 bispecific antibody protein disclosed in PCT application No. PCT/CN2018/075851 (filed on Feb. 8, 2018), and it comprises a fully human anti-PD-1 half antibody and a humanized anti-HER2 half antibody, wherein the heavy chain sequence of the fully human anti-PD-1 half antibody is SEQ ID NO: 12 and SEQ ID NO: 14 in N to C direction, and the light chain sequence is SEQ ID NO: 10 and SEQ ID NO: 4 in N to C direction; the heavy chain sequence of the humanized anti-HER2 half antibody is SEQ ID NO: 6 and SEQ ID NO: 8 in N to C direction, and the light chain sequence is SEQ ID NO: 2 and SEQ ID NO: 4 in N to C direction.

In one embodiment, the anti-PD-1/HER2 bispecific antibody protein is produced by recombinant expression in HEK293 cells or HEK293T, HEK293F or HEK293E cells obtained by modification based on HEK293 cells and in CHO cells or CHO-S, CHO-dhfr⁻, CHO/DG44 or ExpiCHO cells obtained by modification based on CHO cells, and the bispecific antibody protein is purified. Preferably, the antibody in the liquid formulation disclosed herein exhibits significant anti-tumor activity. The anti-PD-1/HER2 bispecific antibody was administered to tumor-bearing mice produced by inoculating immunodeficient NCG mice with HCC1954 human breast cancer cells, and the results show that compared with an anti-PD-1 monoclonal antibody or an anti-HER2 monoclonal antibody, the anti-PD-1/HER2 bispecific antibody has significantly improved anti-tumor activity and can remarkably reduce the tumor volume.

The amount of the anti-PD-1/HER2 bispecific antibody protein in the antibody formulation disclosed herein can vary with the specific desired characteristics of the formulation, the specific environment and the specific purpose for which the formulation is used. In some embodiments, the antibody formulation is a liquid formulation, which may contain about 1-150 mg/mL, preferably about 10-100 mg/mL, e.g., about 10, 20, 30, 40, 50, 60, 70, 80, 90 or 100 mg/mL, anti-PD-1/HER2 bispecific antibody protein.

(ii) Buffer

Buffers are reagents that can control the pH of a solution within an acceptable range. In some embodiments, the buffer in the formulation disclosed herein can control a pH of the formulation disclosed herein at about 5.0-6.5, e.g., about 5.5. In some specific embodiments, the pH of the antibody formulation disclosed herein is about 5.0, 5.2, 5.4, 5.6, 5.8, 6.0, 6.2 or 6.4.

In some embodiments, the buffer in the formulation disclosed herein is selected from histidine, histidine hydrochloride and a combination thereof. In one embodiment, a concentration of the buffer in the liquid antibody formulation disclosed herein is about 5-50 mM. In one embodiment, a concentration of the buffer in the liquid antibody formulation disclosed herein is about 10-30 mM, e.g., about 10, 15, 20, 25 or 30 mM.

In one embodiment, the buffer in the formulation disclosed herein is about 10 mM histidine. In another embodiment, the buffer in the formulation disclosed herein is about 20 mM histidine.

In yet another embodiment, the buffer in the formulation disclosed herein is a combination of about 5.5 mM histidine and about 15 mM histidine hydrochloride.

(iii) Stabilizer

Suitable stabilizers for use in the present invention can be selected from saccharide, polyol and combinations thereof. Further, the stabilizer of the present invention may further comprise an antioxidant.

The saccharide used as the stabilizer may be disaccharide, trisaccharide and polysaccharide, and the saccharide may be selected from, but not limited to: sucrose, dextrose, lactose, maltose, trehalose, cyclodextrin, maltodextrin and glucan. In one embodiment, the saccharide used as the stabilizer is sucrose and/or trehalose.

The polyol used as the stabilizer may be selected from, but not limited to mannitol, sorbitol and xylitol. In one embodiment, the polyol used as the stabilizer is sorbitol.

In some embodiments, the saccharide and/or polyol used as the stabilizer are present in the liquid formulation disclosed herein at a concentration of about 50-500 mM, preferably about 100-400 mM, e.g., about 100, 150, 200, 250, 300, 350 or 400 mM.

Antioxidants that may also be comprised in the stabilizers of the present invention are selected from, but not limited to: homocysteine, cysteine, cystathionine, methionine, glutathione, and peptides comprising any one of homocysteine, cysteine, cystathionine, methionine and glutathione. In the case where an antioxidant is comprised, a total concentration of the stabilizer is about 50-500 mM, preferably about 100-400 mM, e.g., about 100, 150, 200, 250, 300, 350 or 400 mM, wherein a concentration of the antioxidant is about 1-50 mM, preferably about 5-40 mM, e.g., about 5, 10, 20, 30 or 40 mM.

In one embodiment, the liquid formulation disclosed herein comprises sorbitol as the stabilizer. Sorbitol may be present in the liquid formulation disclosed herein in an amount of about 50-400 mM, e.g., about 50, 100, 150, 200, 250, 300, 350 or 400 mM.

In one embodiment, the liquid formulation disclosed herein comprises sucrose as the stabilizer. Sucrose may be present in the liquid formulation disclosed herein in an amount of 50-300 mM, e.g., about 50, 100, 150, 200, 250 or 300 mM.

In one embodiment, the liquid formulation disclosed herein comprises trehalose as the stabilizer. Trehalose may be present in the liquid formulation disclosed herein in an amount of about 50-300 mM, e.g., about 50, 100, 150, 200, 250 or 300 mM.

In one embodiment, the liquid formulation disclosed herein comprises a combination of sucrose and methionine as the stabilizer. In this combination, a total concentration of the stabilizer is about 50-500 mM, preferably about 100-400 mM, e.g., about 100, 150, 200, 250, 300, 350 or 400 mM, wherein a concentration of methionine is about 1-50 mM, preferably about 5-40 mM, e.g., about 5, 10, 20, 30 or 40 mM.

(iv) Surfactant

As used herein, the term "surfactant" refers to an organic substance with an amphiphilic structure; that is, the structure is composed of groups with opposite solubility tendencies, typically an oil-soluble hydrocarbon chain and a water-soluble ionic group.

In one embodiment, the surfactant in the liquid formulation disclosed herein is a non-ionic surfactant, e.g., alkyl poly(ethylene oxide). Specific non-ionic surfactants that can be included in the formulation disclosed herein include, for example, polysorbates such as polysorbate 20, polysorbate 80, polysorbate 60 or polysorbate 40, Pluronic, and the like. In one preferred embodiment, the liquid formulation disclosed herein comprises polysorbate 80 as the surfactant.

The amount of the surfactant in the antibody formulation disclosed herein can vary with the specific desired characteristics of the formulation, the specific environment, and the specific purpose for which the formulation is used. In some preferred embodiments, the formulation can comprise a polysorbate surfactant (e.g., polysorbate 80) at about 0.1-1 mg/mL, preferably about 0.2-0.8 mg/mL, e.g., about 0.2, 0.3, 0.4, 0.5, 0.6, 0.7 or 0.8 mg/mL.

(v) Other Excipients

The liquid antibody formulation disclosed herein may or may not comprise other excipients. For example, the antibody liquid formulation disclosed herein further comprises a tonicity modifier. The tonicity modifier may be selected from the group consisting of sodium acetate, sodium lactate, sodium chloride, potassium chloride and calcium chloride.

These and other known pharmaceutical excipients and/or additives suitable for use in the formulation disclosed herein are well known in the art, for example, as listed in "*The Handbook of Pharmaceutical Excipients,* 4th edition, edited by Rowe et al., American Pharmaceuticals Association (2003); and *Remington: the Science and Practice of Pharmacy,* 21st edition, edited by Gennaro, Lippincott Williams & Wilkins (2005)".

II. Preparation of Formulation

The present invention provides a stable formulation comprising an anti-PD-1/HER2 bispecific antibody protein. The anti-PD-1/HER2 bispecific antibody protein used in the formulation disclosed herein can be prepared using techniques known in the art for the production of antibodies. For example, the anti-PD-1/HER2 bispecific antibody protein can be recombinantly prepared. In one preferred embodiment, the anti-PD-1/HER2 bispecific antibody protein disclosed herein is prepared by recombinant expression in HEK293 cells or HEK293T, HEK293F or HEK293E cells obtained by modification based on HEK293 cells and in CHO cells or CHO-S, CHO-dhfr⁻, CHO/DG44 or ExpiCHO cells obtained by modification based on CHO cells. For example, as described in PCT application No. PCT/CN2018/075851, the anti-PD-1/HER2 bispecific antibody protein is recombinantly prepared.

The use of antibodies as active ingredients in drugs is now very common. Techniques for purifying therapeutic antibodies to pharmaceutical grade are well known in the art. For example, Tugcu et al. (Maximizing productivity of chromatography steps for purification of monoclonal antibodies, *Biotechnology and Bioengineering* 99 (2008) 599-613) describes an antibody three-column purification method in which ion exchange chromatography (anionic IEX and/or cationic CEX chromatography) is used after a protein A capture step. Kelley et al. (Weak partitioning chromatography for anion exchange purification of monoclonal antibodies, *Biotechnology and Bioengineering* 101 (2008) 553-566) describes a two-column purification method in which a weak partitioning anion exchange resin is used after protein A affinity chromatography.

Generally, antibodies recombinantly produced can be purified using conventional purification methods to provide a drug substance with sufficient reproducibility and moderate purity for formulating antibody formulations. For example, after the antibody is secreted from the recombinant expression cells into the culture medium, the supernatant from the expression system can be concentrated using a commercially available protein concentration filter, e.g., Amicon ultrafiltration device. Then the antibody can be purified by methods such as chromatography, dialysis, and affinity purification. Protein A is suitable as an affinity ligand for the purification of as IgG1, IgG2 and IgG4 antibodies. Other antibody purification methods, such as ion exchange chromatography, can also be used. After the antibody with sufficient purity is obtained, a formulation comprising the antibody can be prepared according to methods known in the art.

For example, the preparation can be performed by the following steps: (1) removing impurities such as cells from fermentation broth by centrifuging and clarifying after the fermentation to obtain a supernatant; (2) capturing an antibody using affinity chromatography (e.g., a protein A column with specific affinity for IgG1, IgG2 and IgG4 antibodies); (3) inactivating viruses; (4) purifying (usually CEX cation exchange chromatography can be adopted) to remove impurities in a protein; (5) filtering the viruses (to reduce the virus titer by, e.g., more than 4 log 10); and (6) ultrafiltering/diafiltering (which can be used to allow the protein to be exchanged into a formulation buffer that is favorable for its stability and concentrated to a suitable concentration for injection). See, e.g., B. Minow, P. Rogge, K. Thompson, *BioProcess International*, Vol. 10, No. 6, 2012, pp. 48-57.

III. Analytical Method of Formulation

During the storage of antibody formulations, antibodies may undergo aggregation, degradation or chemical modification, resulting in antibody heterogeneity (including size heterogeneity and charge heterogeneity), aggregates and fragments, etc., which may affect the quality of the antibody formulations. Accordingly, it is necessary to monitor the stability of antibody formulations.

Various methods are known in the art for testing the stability of antibody formulations. For example, the purity of the antibody formulation can be analyzed and the aggregation level of the antibody can be evaluated by methods such as reduced CE-SDS, non-reduced CE-SDS and SEC-HPLC; charge variants in the antibody formulation can be analyzed by capillary isoelectric focusing electrophoresis (cIEF), imaged capillary isoelectric focusing (iCIEF), ion exchange chromatography (IEX), and the like. In addition, the stability of the formulation can be determined quickly by visually inspecting the appearance of the formulation. The change in turbidity of the formulation can also be detected by the $OD_{350 \ nm}$ method, which gives information about the amount of soluble and insoluble aggregates. In addition, the change in protein content in the formulation can be detected by the ultraviolet spectrophotometry method (UV method).

Non-reduced CE-SDS is a method for determining the purity of antibodies using a capillary as a separation channel. In CE-SDS, protein migration is driven by the surface charge caused by SDS binding, which is proportional to the molecular weight of the protein. Since all SDS-protein complexes have similar mass-to-charge ratios, electrophoretic separation based on the size or hydrodynamic radius of the molecules can be achieved in the molecular sieve gel matrix of the as capillary. This method has been widely used to monitor the purity of denatured intact antibodies. Generally, in non-reduced CE-SDS, the test sample is mixed with an SDS sample buffer and iodoacetamide. Then the mixture can be incubated at 68-72° C. for about 10-15 min and cooled to room temperature before the supernatant is centrifuged for analysis. The protein migration is detected using an ultraviolet detector to obtain an electropherogram. The purity of the antibody formulation can be calculated as the percentage of the IgG main peak area to the sum of all peak areas. For further description of CE-SDS, see, e.g., Richard R. et al., Application of CE SDS gel in development of biopharmaceutical antibody-based products, *Electrophoresis,* 2008, 29, 3612-3620.

Size exclusion-high performance liquid chromatography (SEC-HPLC) is another important method for the standardization and quality control of antibodies. In this method, molecules are separated mainly based on the differences in their size or hydrodynamic radius. Antibodies can be separated in three main forms by SEC-HPLC: high-molecular-weight species (HMMS), main peak (mainly antibody monomer), and low molecular-weight species (LMMS). The purity of the antibody can be calculated as the percentage of the main peak area to the sum of all peak areas on the chromatogram. The percentage of antibody monomer in the formulation can be measured by SEC-HPLC, which gives information about the content of soluble aggregates and splices. For further description of SEC-HPLC, see, e.g., *J. Pharm. Scien.,* 83:1645-1650, (1994); *Pharm. Res.,* 11:485 (1994); *J. Pharm. Bio. Anal.,* 15:1928 (1997); *J. Pharm. Bio. Anal.,* 14:1133-1140 (1986). In addition, see also, e.g., R. Yang et al., High resolution separation of recombinant monoclonal antibodies by size exclusion ultra-high performance liquid chromatography (SE-UHPLC), *Journal of Pharmaceutical and Biomedical Analysis* (2015), dx.doi.org/10.1016/j.jpba.2015.02.032; and Alexandre Goyon et al., Protocols for the analytical characterization of therapeutic monoclonal antibodies, I-Non-denaturing chromatographic techniques, *Journal of Chromatography,* dx.doi.org/10.1016/j.jchromb.2017.05.010.

Imaged capillary isoelectric focusing (iCIEF) can be used to analyze the charge heterogeneity of antibodies. This method can provide quantitative distribution of charge variants. In iCIEF, molecules are separated based on the difference in their charge in a pH gradient (apparent pI value). In iCIEF, the separation column is typically a short capillary (e.g., silica capillary, 5 cm length, 100 μm I.D.), the proteins are focused in the capillary column at high voltage, and the focusing is monitored online in real time by a whole column imaging detection system operating at 280 nM. One advantage of this technique is that various charge variants of an antibody sample can be simultaneously recorded by the whole column detection system. Generally, in iCIEF, the sample is as mixed with urea and an iCIEF buffer containing methylcellulose, pI molecular weight standards and ampholytes. Then after the sample has been focused for a period of time on an iCIEF analyzer, such as an iCE280 analyzer (Protein Simple, Santa Clara, CA.), using an iCIEF column, such as a ProtionSimple assembled iCIEF column, the absorbance at 280 nm is measured to obtain a spectrum of charge variants of the focused antibody. In the iCIEF spectrum, protein-related peaks eluted before the main peak (i.e., principal component) are classified as acidic components, while protein-related peaks eluted after the main peak are classified as basic components. The relative amounts of the principal component, acidic component and basic component can be expressed as a percentage to the total peak area. For further description of iCIEF, see, e.g., Salas-Solano O et al., Robustness of iCIEF methodology for the analysis of monoclonal antibodies: an interlaboratory study, *J Sep Sci.* 2012 November; 35(22):3124-9. doi: 10.1002/jssc.201200633. Epub 2012 Oct. 15; and Dada O O et al., Characterization of acidic and basic variants of IgG1 therapeutic monoclonal antibodies based on non-denaturing IEF fractionation, *Electrophoresis.* 2015 November; 36(21-22): 2695-2702. doi: 10.1002/elps.201500219. Epub 2015 Sep. 18.

The charge variants of the antibody in the antibody formulation can also be determined by cation exchange high performance liquid chromatography (CEX-HPLC). In this method, peaks eluted from the CEX-HPLC column earlier than the retention time of the main peak are labeled as "acidic peaks", while those eluted from the CEX-HPLC column later than the retention time of the main peak are labeled as "basic peaks".

Accelerated stability studies can be used to check the stability of products, which facilitates the screening of stable pharmaceutical formulations. For example, formulation samples can be placed at an elevated temperature, e.g., about 40±2° C. or 25±2° C., for an accelerated stability study. The test indexes can include appearance, visible particles, protein content, turbidity, purity (SEC-HPLC and non-reduced CE-SDS) and charge variants (iCIEF and CEX-HPLC).

In addition, the efficacy or biological activity of the antibody can be detected. For example, the ability of an antibody in a formulation to bind to its antigenic molecules (HER2 molecule and PD-1 molecule) can be tested. Various methods are known to those skilled in the art for quantifying the specific binding of an antibody to an antigen, such as immunoassay, e.g., ELISA.

The anti-PD-1/HER2 bispecific antibody protein formulation disclosed herein is stable. In one embodiment, the purity of the anti-PD-1/HER2 bispecific antibody protein in the antibody formulation disclosed herein is at least 90%, 91%, 92%, 93%, 94%, 95%, 96%, 97%, 98%, or 99% or higher after storage at about 5° C., 25° C., 37° C., 40° C. or 45° C. for at least 1 month, 2 months or 3 months, e.g., after storage at 5±3° C. for 3 months, as measured by size exclusion chromatography or non-reduced CE-SDS. In one embodiment, at least 60%, preferably at least 65%, of the anti-PD-1/HER2 bispecific antibody protein in the antibody formulation disclosed herein is in non-basic and non-acidic forms (i.e., the main peak or principal charge form) after storage at about 5° C., 25° C., 37° C., 40° C. or 45° C. for at least 1 month, 2 months or 3 months, e.g., after storage at 5±3° C. for 3 months, as measured by iCIEF.

IV. Use of Formulation

The antibody formulation comprising an anti-PD-1/HER2 bispecific antibody protein disclosed herein can be used for treating, preventing or delaying various diseases or disorders associated with the HER2 signaling pathway and/or the PD-1 signaling pathway. "Diseases or disorders associated with the HER2 signaling pathway" and/or "diseases or disorders associated with the PD-1 signaling pathway" refer herein to diseases or disorders that can be treated (e.g., ameliorated) or prevented with the anti-PD-1/HER2 bispecific antibody protein formulation disclosed herein. Any disease or disorder that can benefit from the treatment with the antibody formulation disclosed herein is suitable for the present invention.

The formulation comprising an anti-PD-1/HER2 bispecific antibody protein disclosed herein can be used to prevent or treat various blood diseases and solid tumors, including but not limited to leukemia, lymphoma, myeloma, brain tumor, head and neck squamous cell carcinoma, non-small cell lung cancer, nasopharyngeal cancer, esophageal cancer, gastric cancer, pancreatic cancer, gall bladder cancer, cholangiocarcinoma, liver cancer, colorectal cancer, breast cancer, ovarian cancer, cervical cancer, endometrial cancer, uterine sarcoma, prostatic cancer, bladder cancer, renal cell carcinoma and melanoma.

The present invention also provides use of the formulation disclosed herein in preparing a medicament for delivering the anti-PD-1/HER2 bispecific antibody protein to a mammal, or for treating, preventing or ameliorating one or more of the diseases and disorders described above. Preferably, the mammal is a human.

The antibody formulation disclosed herein can be administered to a subject or a patient in a variety of pathways. For example, administration can be performed by infusion or by using a syringe. Accordingly, in one aspect, the present invention provides a delivery device (e.g., a syringe) comprising the antibody formulation disclosed herein (e.g., a pre-filled syringe). The patient will receive an effective amount of the anti-PD-1/HER2 bispecific antibody protein as the primary active ingredient, i.e., an amount sufficient to treat, ameliorate or prevent the disease or disorder of interest.

The therapeutic effect can include a reduction in physiological symptoms. The optimal effective amount and concentration of the antibody for any specific subject will depend on a variety of factors including the age, weight, health status and/or sex of the patient, the nature and extent of the disease, the activity of the specific antibody, its clearance by the body, as well as any other possible treatments administered in combination with the antibody formulation. For a specific case, the effective amount delivered can be determined based on the judgment of a clinician. Depending on the indication to be treated, an effective dose can range from about 0.005 mg/kg body weight to about 50 mg/kg body weight, or from about 0.1 mg/kg body weight to about 20 mg/kg body weight. In this aspect, the use of known antibody-based drugs can provide some guidance. The dosage can be a single-dose regimen or a multi-dose regimen.

The following examples are described to assist in understanding the present invention. The examples are not intended to be and should not be interpreted in any way as limiting the protection scope of the present invention.

Abbreviations

CE-SDS: capillary electrophoresis-sodium dodecyl sulfate

ELISA: enzyme-linked immunosorbent assay iCIEF: imaged capillary isoelectric focusing SEC-HPLC: size exclusion-high performance liquid chromatography

EXAMPLES

In order to develop a formulation formula for long-term stable storage of a recombinant anti-programmed death receptor 1 (PD-1) and anti-human epidermal growth factor receptor 2 (HER2) bispecific antibody injection and to ensure that the quality of the product is controllable over its shelf life (at least 24 months), a formula screening test is designed to examine the effect of different excipients on the stability of the anti-PD-1/HER2 bispecific antibody formulation. The materials and methods used for the tests are as follows:

Materials and Methods 1.1. Materials Used in Formulation Research of Present Invention

| Name | Grade | Manufacturer & site | Catalog No. | Criteria |
| --- | --- | --- | --- | --- |
| Histidine | Pharmaceutical grade | Ajinomoto, Shanghai | N/A | *Ch. P* (2015 Edition) |
| Histidine hydrochloride | Pharmaceutical grade | Ajinomoto, Shanghai | N/A | *Ch. P* (2015 Edition) |
| Sorbitol | Pharmaceutical grade | Roquette, French | H20110265 | *EP, BP, NF, USP* |
| Sucrose | Pharmaceutical grade | Merck, Germany | 1.00892.9050 | *Ch. P* (2015 Edition), *USP* |
| Trehalose | Pharmaceutical grade | Pfanstiehl, USA | T-104-4 | *USP/NF, EP, JP* |
| Methionine | Pharmaceutical grade | Bafeng, Hubei | N/A | *Ch. P* (2015 Edition) |
| Polysorbate 80 | Pharmaceutical grade | Well, Nanjing | Jiangsu MPA Approval No. F15423203 | *Ch. P* (2015 Edition) |
| Hydrochloric acid | Pharmaceutical grade | Merck, Germany | 1.00314.2508 | *Ph Eur, BP, JP, NF* |

Note:
N/A denotes "Not applicable".

1.2. Instruments and Equipment

| Name | Manufacturer & site | Model No. | No. |
| --- | --- | --- | --- |
| Constant temperature and humidity chamber | BINDER, Germany | KBF P 720 | PD-A1-069 |
| Biochemical incubator | Jinghong, Shanghai | SHP-150 | PD-A1-200 |
| Vortex mixer | VWR, USA | DVX-2500 | PD-A1-140 |
| Medical refrigerator | Haier, Qingdao | HYC-360 | PD-A1-166 |
| Ultra-low temperature refrigerator | Thermo, USA | 907 | PD-A1-175 |
| Clarity detector | Tianda Tianfa, Tianjin | YB-2 | PD-A1-033 |
| Ultraviolet-visible spectrophotometer | Shimadzu, Japan | UV-1800 | AS-A1-037 |
| pH meter | Mettler, Switzerland | S220/FE20 | PD-A1-002 |
| Multi-channel microspectrophotometer | Thermo, USA | Nanodrop8000 | PD-A1-052 |
| Benchtop refrigerated centrifuge | Thermo, USA | SL16R | PD-A1-082 |
| Clean bench | Antai Airtech, Suzhou | SW-CJ-2FD | QC-A1-011 |
| Insoluble particle detector | Tianda Tianfa, Tianjin | GWJ-8 | QC-A1-094 |

1.3. Test Items and Methods for Formulation Stability

The antibody formulation was tested for the following items: (1) the appearance and the presence of visible particles; (2) the protein content in the formulation determined by the ultraviolet method (UV method); (3) the turbidity determined by detecting absorbance at 350 nm; (4) the purity of the antibody formulation determined by size exclusion chromatography (e.g., size exclusion high performance liquid chromatography (SEC-HPLC)) and expressed as the percentage of the monomer area to the sum of all peak areas; (5) the purity of the antibody formulation determined by reduced capillary electrophoresis-sodium dodecyl sulfate (reduced CE-SDS) and/or non-reduced capillary electrophoresis-sodium dodecyl sulfate (non-reduced CE-SDS) and expressed as the percentage of the monomer area to the sum of all peak areas; (6) charge variants in the antibody formulation determined by imaged capillary isoelectric focusing (iCIEF) and expressed as the percentages of the principal component, acidic component and basic component; and (7) the relative binding activity of the anti-PD-1/HER2 bispecific antibody in the antibody formulation to antigens PD-1 and HER2 determined by immunoassay, e.g., direct ELISA.

Detection of Visible Particles

The visible particles in the sample were detected using a clarity detector (model No. YB-2, Tianda Tianfa, Tianjin) according to the method described in the National Pharmacopoeia Committee, the *Pharmacopoeia of the People's Republic of China* (2015 edition, volume IV General Rules 0904 "Test for Visible Particles"), Beijing, China Medical Science Press, 2015.

Determination of Protein Content

The protein content in the sample was determined using an ultraviolet spectrophotometer (model No. UV-1800, Shimadzu, Japan).

Determination of Turbidity

The turbidity of the sample was determined by measuring the absorbance at 350 nm using an ultraviolet spectrophotometer (model No. UV-1800, Shimadzu, Japan).

Purity (SEC-HPLC)

Separation was performed using an SEC column with a phosphate buffer (3.12 g of sodium dihydrogen phosphate dihydrate, 8.77 g of sodium chloride and 34.84 g of arginine were dissolved in ultra-pure water, the pH was adjusted to 6.8 by adding hydrochloric acid, and the volume was brought to 1000 mL) as the mobile phase. The chromatographic column protective solution was 0.05% (w/v) $NaN_3$, the sample injection volume was 50 μL, the flow rate was 0.5 mL/min, the collection time was 30 min, the column temperature was 25° C., and the detection wavelength was 280 nm. A sample was diluted to 2 mg/mL with ultra-pure water for use as a sample solution. A formulation buffer was diluted in the same manner as described above to prepare a blank solution. The blank solution and the sample solution were separately injected into a liquid chromatograph in as an amount of 50 μL for the determination.

Purity (Reduced CE-SDS)

The determination was conducted by capillary gel electrophoresis. The capillary was an uncoated capillary having an inner diameter of 50 μm, a total length of 30.2 cm and an effective length of 20.2 cm. Before electrophoresis, the capillary column was washed with 0.1 mol/L sodium hydroxide, 0.1 mol/L hydrochloric acid, ultra-pure water, and electrophoresis gel at 70 psi. The sample was diluted to 2.0 mg/mL with an appropriate amount of ultra-pure water. 50 μL of the diluted sample was transferred into a 1.5-mL centrifuge tube, and 45 μL of sample buffer at pH 6.5 (0.32 g of citric acid monohydrate and 2.45 g of disodium phosphate dodecahydrate were dissolved in 45 mL of ultra-pure water, and the volume was brought to 50 mL to prepare a citrate-phosphate at buffer; 80 μL of 10% (w/v) sodium dodecyl sulfate solution was added to 200 μL of the buffer, the volume was brought to 1 mL with water, and the mixture was well mixed to obtain the sample buffer), 1 μL of internal standard (10 kDa protein, 5 mg/mL; Beckman Coulter, Catalog No. 390953) and 5 μL of β-mercaptoethanol were added. The mixture was well mixed, heated at 70±2° C. for 10±2 min, cooled to room temperature, and transferred to a sample bottle for future use as a sample solution. A formulation buffer of the same volume as the sample was processed by the same method as above to prepare the blank solution. Conditions for sample injection: −5 kV for 20 s; separation voltage: −15 kV for 35 min. The capillary column temperature was controlled at 25° C. and the detection wavelength was 220 nm.

Purity (Non-Reduced CE-SDS)

The determination was conducted by capillary gel electrophoresis. The capillary was an uncoated capillary having an inner diameter of 50 μm, a total length of 30.2 cm and an effective length of 20.2 cm. Before electrophoresis, the capillary column was washed with 0.1 mol/L sodium hydroxide, 0.1 mol/L hydrochloric acid, ultra-pure water, and electrophoresis gel at 70 psi. A sample was diluted to 2.0 mg/mL with an appropriate amount of ultra-pure water. 50 μL of the diluted sample was transferred into a 1.5-mL centrifuge tube, and 45 μL of sample buffer at pH 6.5 (0.32 g of citric acid monohydrate and 2.45 g of disodium phosphate dodecahydrate were dissolved in 45 mL of ultra-pure water, and the volume was brought to 50 mL to prepare a citrate-phosphate buffer; 80 μL of 10% (w/v) sodium dodecyl sulfate solution was added to 200 μL of the buffer, the volume was brought to 1 mL with water, and the mixture was well mixed to obtain the sample buffer), 1 μL of internal standard (10 kDa protein, 5 mg/mL; Beckman Coulter, Catalog No. 390953) and 5 μL of 250 mmol/L NEM solution (62 mg of N-ethylmaleimide was dissolved in 2 mL of ultra-pure water) were added. The mixture was well mixed, heated at 70±2° C. for 10±2 min, cooled to room temperature, and transferred to a sample bottle for future use as a sample solution. A formulation buffer of the same volume as the sample was processed by the same method as above to prepare the blank solution. Conditions for sample injection: −5 kV for 20 s; separation voltage: −15 kV for 35 min. The capillary column temperature was controlled at 25° C. and the detection wavelength was 220 nm.

Charge Variants (iCIEF)

The determination was conducted by imaged capillary isoelectric focusing (iCIEF). The inner diameter of the capillary was 100 μm, and the total length was 5 cm. The capillary column was rinsed with 0.5% methylcellulose solution (hereinafter abbreviated as MC solution) and ultra-pure water before electrophoresis. The sample was injected in vacuum, the pre-focusing was conducted at 1.5 kV for 1 min, the focusing was conducted at 3 kV for 8 min, the sample injection time was 55 s, the temperature of the sample tray was 10° C., and the detection wavelength was 280 nm. The cathodic stabilizer was 500 mmol/L arginine solution, and 0.5% MC solution was added to decrease the adhesion between the protein and the capillary. The sample was diluted to 1.0 mg/mL with water, 20 μL of the diluted sample was added to 78 μL of a premixed solution (the mixture ratio of the premixed solution is as follows: 70 μL of pI 0.5% MC solution, 4 μL of ampholyte (pH 3-10), 2 μL of cathodic stabilizer, 1 μL of pI 5.85 marker and 1 μL of pI 9.99 marker), and the mixture was well mixed to prepare a sample solution. The sample solution was injected for analysis, and the content of the principal component, the acidic component and the basic component was calculated according to an area normalization method.

Relative Binding Activity (Direct ELISA)

Antigen (for detection of the relative binding activity of an anti-PD-1 end of an anti-PD-1/HER2 bispecific antibody to PD-1, recombinant human PD-1 from Sinobiological (Catalog No.: 10377-H08H) was used; for detection of the relative binding activity of an anti-HER2 end of an anti-PD-1/HER2 bispecific antibody to HER2, human HER2/ErbB2 protein (His tag) from Sinobiological (Catalog No.: 10004-H08H-100) was used) was diluted to 0.5 μg/mL with CBS, and then coated on a 96-well microplate at 100 μL/well and incubated at 4° C. overnight. After being washed, the plate was blocked with a blocking solution (2% BSA-PBST, 300 μL/well) at 37° C. for 2 h. The anti-PD-1/HER2 bispecific antibody was diluted to 3 μg/mL with 2% BSA-PBST and a 3-fold serial dilution was performed to obtain 11 concentrations (0.05-3000 ng/mL). The sample serially diluted was added, at 100 μL/well, into the microplate with the blocking solution discarded. For negative control wells, only 100 μL of the diluent (2% BSA-PBST) was added. The plate was incubated in a thermostatic incubator at 37° C. for 60 min. After the plate was washed, HRP-conjugated goat anti-human IgG-Fc fragment (BETHYL, USA, Catalog No.: A80-104P) diluted with 2% BSA-PBST was added as a secondary antibody (100000-fold dilution, 100 μL/well) for reaction at 37° C. for 30 min. After the plate was washed, 100 μL of TMB chromogenic solution was added, and after 10 min of chromogenic reaction, 100 μL of 1 mol/L $H_2SO_4$ was added to each well to terminate the reaction. The OD value at 450 nm was measured with 620 nm being the reference wavelength. By taking concentration values of the sample at all concentration gradients as an abscissa and the $OD_{450\ nm}$-$OD_{620\ nm}$ values of the sample at all concentration gradients as an ordinate, $EC_{50}$ values were calculated by Prism four-parameter fitting to reflect the binding activity of the antibody to each antigen.

Example 1

Preparation and Purification of Anti-PD-1/HER2 Bispecific Antibody

An anti-PD-1/HER2 bispecific antibody was prepared and purified as described in PCT application No. PCT/CN2018/075851.

Specifically, X0GC expression vectors containing the heavy chain and light chain of an anti-human PD-1 antibody, respectively, were constructed (see Chinese Patent Application No. 200780038403.3 for construction of X0GC expression vectors), wherein the nucleotide sequence of the light chain variable region is set forth in SEQ ID NO: 9, and the amino acid sequence is set forth in SEQ ID NO: 10; the nucleotide sequence of the light chain constant region is set forth in SEQ ID NO: 3, and the amino acid sequence is set forth in SEQ ID NO: 4; the nucleotide sequence of the heavy chain variable region is set forth in SEQ ID NO: 11, and the amino acid sequence is set forth in SEQ ID NO: 12; the nucleotide sequence of the heavy chain constant region is set forth in SEQ ID NO: 13, and the amino acid sequence is set forth in SEQ ID NO: 14.

X0GC expression vectors containing the heavy chain and light chain of an anti-human HER2 antibody, respectively, were constructed, wherein the nucleotide sequence of the light chain variable region is set forth in SEQ ID NO: 1, and the amino acid sequence is set forth in SEQ ID NO: 2; the nucleotide sequence of the light chain constant region is set forth in SEQ ID NO: 3, and the amino acid sequence is set forth in SEQ ID NO: 4; the nucleotide sequence of the heavy chain variable region is set forth in SEQ ID NO: 5, and the amino acid sequence is set forth in SEQ ID NO: 6; the nucleotide sequence of the heavy chain constant region is set forth in SEQ ID NO: 7, and the amino acid sequence is set forth in SEQ ID NO: 8.

The expression vectors containing the heavy chain and light chain of the anti-human PD-1 antibody, respectively, were transfected into 293F cells (FreeStyle™ 293-F Cells, Catalog No.: R79007, Invitrogen), and then expressing, purifying and reducing processes were performed, thus obtaining an anti-human PD-1 half antibody molecule containing one heavy chain and one light chain.

Similarly, the expression vectors containing the heavy chain and light chain of the anti-human HER2 antibody, respectively, were transfected into 293F cells (FreeStyle™ 293-F Cells, Catalog No.: R79007, Invitrogen), and then expressing, purifying and reducing processes were performed to obtain an anti-human HER2 half antibody molecule containing one heavy chain and one light chain.

The reduced anti-PD-1 half antibody molecule and the reduced anti-HER2 half antibody molecule were mixed at an equimolar ratio and the mixture was subjected to a recombination reaction at 4° C. for 24 h to obtain a solution of a bispecific antibody comprising heterodimers of the anti-PD-1 half antibody molecule and the anti-HER2 half antibody molecule. The solution was concentrated by ultrafiltration using an ultrafiltration concentration tube, and then purified at 4° C. using an AKTA explorer 100 type protein purification system (GE Healthcare) and an ion chromatography column Source 15S (16 mm I.D., 17 mL, GE Healthcare), thus obtaining an anti-PD-1/HER2 bispecific antibody with a purity of 99.96%.

Example 2

Test for Effect of pH on Stability of Formulation (I)

This example examines the stability of formulations comprising an anti-PD-1/HER2 bispecific antibody at pH 5.0-6.5. A total of 4 pH values were designed, namely 5.0, 5.5, 6.0 and 6.5.

2.1. Experimental Procedures 10 mM histidine-5% (w/v) sorbitol buffer was prepared, and the pH was adjusted to 5.0, 5.5, 6.0 and 6.5 with diluted hydrochloric acid. The purified anti-PD-1/HER2 bispecific antibody obtained in Example 1 was exchanged into solutions of the different pH values by ultrafiltration. The content of the bispecific antibody protein in the samples was adjusted to about 20 mg/mL after the exchange, and then polysorbate 80 was added until the final concentration of polysorbate 80 was 0.30 mg/mL. The solutions were filtered and aliquoted into vials, followed by plugging and capping. The stability of the samples was examined at 40±2° C. and the specific experimental scheme is shown in Table 1.

TABLE 1

| Experimental scheme | | | | | |
| --- | --- | --- | --- | --- | --- |
| Experimental | Sampling time points | | | | |
| conditions | Day 0 | Week 1 | Week 2 | Month 1 | Test items |
| 40° C. ± 2° C. | X | X | X | X | Appearance, visible particles, protein content, turbidity, purity (SEC-HPLC and CE-SDS), charge variants (iCIEF) and relative binding activity (direct ELISA) |

Note:
(1) x represents that sampling is performed at this time point. (2) After sampling at these time points, the obtained samples were first put into an ultra-low temperature refrigerator and frozen at −80° C. for later detection, and then thawed for detection as required.

2.2. Criteria

According to the knowledge of the product and the precision of the instrument and the method, criteria for determining the absence of changes in sample test indexes as compared to initial values were set, so as to determine whether the sample changed, as detailed in Table 2.

TABLE 2

| Criteria for absence of quality change | |
| --- | --- |
| Test items | Criteria for absence of change |
| Appearance (visual inspection) | Clear to slightly opalescent, colorless to pale yellow liquid, no particles |
| Visible particles (Test for visible particles) | Conforms to the General Rule 0904 of the *Pharmacopoeia of the People's Republic of China* (2015 edition, volume IV) |
| Protein content (UV method) | Change rate ≤10% |
| Turbidity (OD$_{350\ nm}$ method) | Change value ≤0.02 |
| Purity (SEC-HPLC) | Change in main peak purity ≤1% |
| Purity (reduced CE-SDS) | Change in main peak purity ≤2% |
| Purity (non-reduced CE-SDS) | Change in main peak purity ≤2% |
| Charge variants (iCIEF) | Changes in principal component, acidic component and basic component ≤2% |
| Relative binding activity (direct ELISA) | 70~130% |

2.3. Experimental Results of Formula Screening Test (I)

(1) Appearance and Visible Particles

After storage at 40±2° C. for one month, the samples at pH 5.0, 5.5, 6.0 and 6.5 were up to standard in terms of appearance and visible particles.

(2) Protein Content

Detection results of the protein content of the samples at pH 5.0, 5.5, 6.0 and 6.5 after storage at 40±2° C. for different time periods are shown in Table 3. The results show that the samples at each pH did not significantly change after storage at 40±2° C. for 1 month.

TABLE 3

| Protein content of samples at pH 5.0, 5.5, 6.0 and 6.5 after storage at 40 ± 2° C. for different time periods (UV method, mg/mL) | | | |
| --- | --- | --- | --- |
| Sample | Time | | |
| name | Day 0 | Week 1 | Week 2 | Month 1 |
| pH 5.0 | 20.7 | 20.4 | 20.1 | 20.5 |
| pH 5.5 | 20.6 | 20.7 | 20.1 | 20.7 |
| pH 6.0 | 20.8 | 20.7 | 20.6 | 20.7 |
| pH 6.5 | 20.5 | 20.7 | 20.3 | 20.9 |

(3) Turbidity

Figure 2:
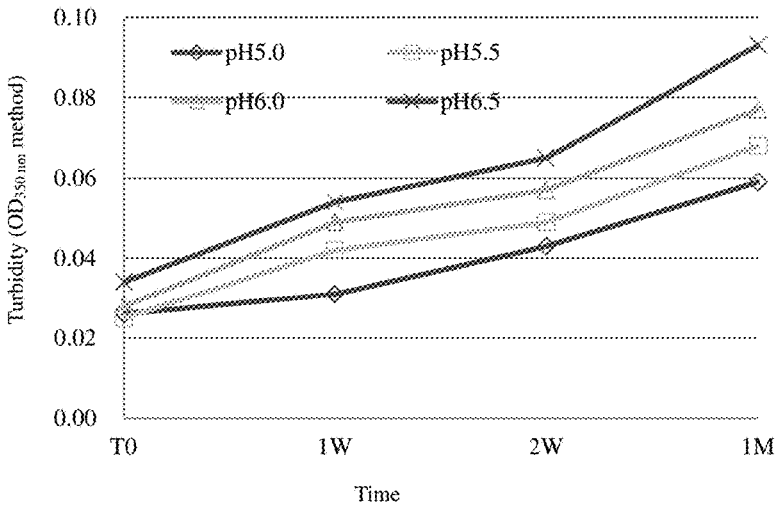
FIG. 2 shows the trend of change in the turbidity of the samples of the anti-PD-1/HER2 bispecific antibody formulation at pH 5.0, 5.5, 6.0 and 6.5 after storage at 40±2° C. for different time periods, as determined by the $OD_{350\ nm}$ method. On the abscissa, T0 represents day 0, 1W represents 1 week, 2W represents 2 weeks, and 1M represents 1 month.

Detection results of the turbidity of the samples at pH 5.0, 5.5, 6.0 and 6.5 after storage at 40±2° C. for different time periods are shown in Table 4, and its trend of change is shown in FIG. 2. The results show that the turbidity of the samples at each pH increased after storage at 40±2° C. for 1 month, and the higher the pH, the greater the turbidity change rate.

TABLE 4

| Turbidity of samples at each pH after storage at 40 ± 2° C. for different time periods (OD$_{350\ nm}$ method) | | | |
| --- | --- | --- | --- |
| Sample | Time | | |
| name | Day 0 | Week 1 | Week 2 | Month 1 |
| pH 5.0 | 0.026 | 0.031 | 0.043 | 0.059 |
| pH 5.5 | 0.025 | 0.042 | 0.049 | 0.068 |
| pH 6.0 | 0.028 | 0.049 | 0.057 | 0.077 |
| pH 6.5 | 0.034 | 0.054 | 0.065 | 0.093 |

(4) Purity

Figure 3:
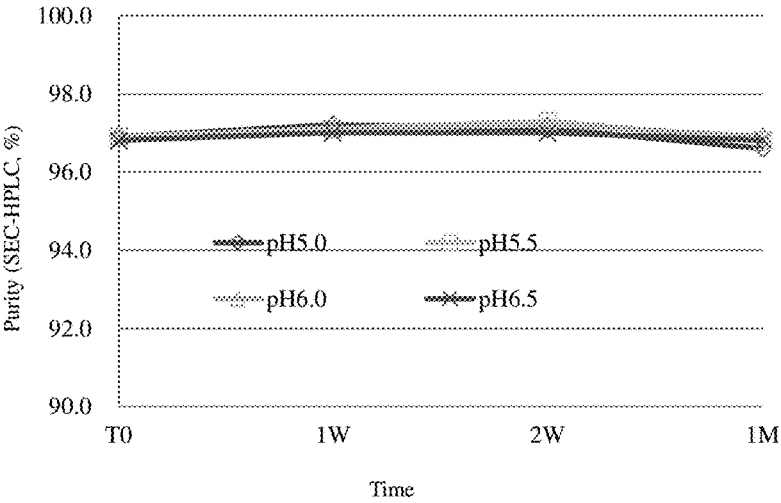
FIG. 3 shows the trend of change in the protein purity of the samples of the anti-PD-1/HER2 bispecific antibody formulation at pH 5.0, 5.5, 6.0 and 6.5 after storage at 40±2° C. for different time periods, as determined by SEC-HPLC. On the abscissa, T0 represents day 0, 1W represents 1 week, 2W represents 2 weeks, and 1M represents 1 month.

After storage at 40±2° C. for different time periods, the protein purity of the samples at pH 5.0, 5.5, 6.0 and 6.5 was determined by SEC-HPLC. The results are shown in Table 5, and the trend of change is shown in FIG. 3. The results show that the purity of the samples at each pH did not significantly change after examination at 40±2° C. for 1 month.

TABLE 5

| Protein purity of samples determined by SEC-HPLC (%) | | | |
| --- | --- | --- | --- |
| Sample | Time | | |
| name | Day 0 | Week 1 | Week 2 | Month 1 |
| pH 5.0 | 96.9 | 97.2 | 97.1 | 96.6 |
| pH 5.5 | 96.9 | 97.1 | 97.3 | 96.8 |
| pH 6.0 | 96.9 | 97.1 | 97.2 | 96.9 |
| pH 6.5 | 96.8 | 97.0 | 97.0 | 96.8 |

Figure 4:
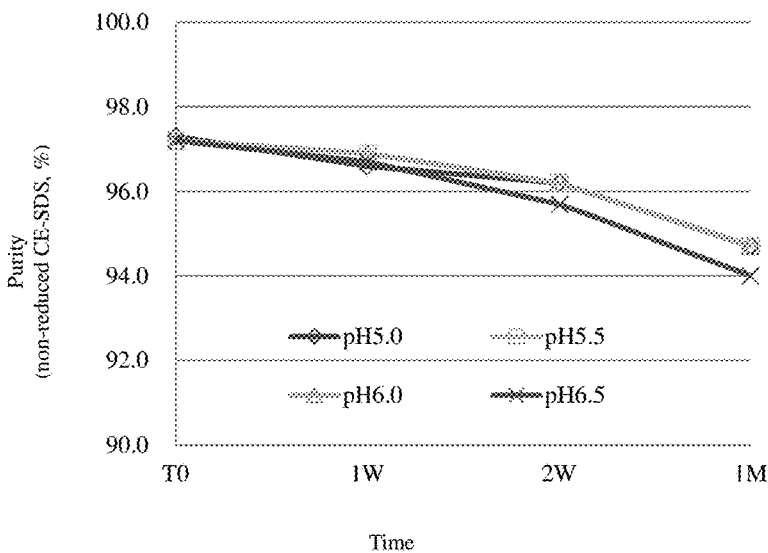
FIG. 4 shows the trend of change in the protein purity of the samples of the anti-PD-1/HER2 bispecific antibody formulation at pH 5.0, 5.5, 6.0 and 6.5 after storage at 40±2° C. for different time periods, as determined by non-reduced CE-SDS. On the abscissa, T0 represents day 0, 1W represents 1 week, 2W represents 2 weeks, and 1M represents 1 month.

After storage at 40±2° C. for different time periods, the protein purity of the samples at pH 5.0, 5.5, 6.0 and 6.5 was determined by non-reduced CE-SDS. The results are shown in Table 6, and the trend of change is shown in FIG. 4. The results show that after examination at 40±2° C. for 1 month, the purity values of the samples at each pH were reduced by 2.6%, 2.5%, 2.5% and 3.2%, respectively, compared with the purity of the sample at day 0.

TABLE 6

| Protein purity of samples determined by non-reduced CE-SDS (%) | | | |
| --- | --- | --- | --- |
| Sample | Time | | |
| name | Day 0 | Week 1 | Week 2 | Month 1 |
| pH 5.0 | 97.3 | 96.6 | 96.2 | 94.7 |
| pH 5.5 | 97.2 | 96.9 | 96.2 | 94.7 |
| pH 6.0 | 97.2 | 96.9 | 96.2 | 94.7 |
| pH 6.5 | 97.2 | 96.7 | 95.7 | 94.0 |

Figure 5:
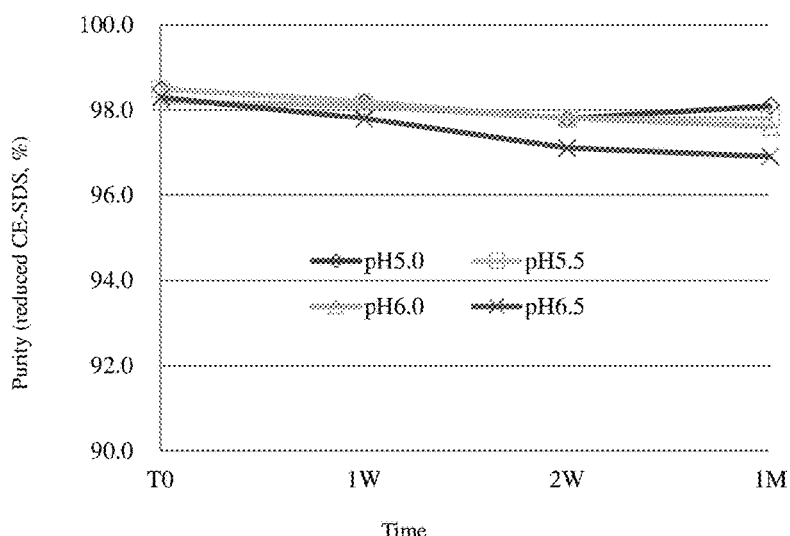
FIG. 5 shows the trend of change in the protein purity of the samples of the anti-PD-1/HER2 bispecific antibody formulation at pH 5.0, 5.5, 6.0 and 6.5 after storage at 40±2° C. for different time periods, as determined by reduced CE-SDS. On the abscissa, T0 represents day 0, 1W represents 1 week, 2W represents 2 weeks, and 1M represents 1 month.

After storage at 40±2° C. for different time periods, the protein purity of the samples at pH 5.0, 5.5, 6.0 and 6.5 was determined by reduced CE-SDS. The results are shown in Table 7, and the trend of change is shown in FIG. 5. The results show that after examination at 40±2° C. for 1 month, the purity values of the samples at each pH were reduced by 0.4%, 0.7%, 0.6% and 1.4%, respectively, compared with the purity of the sample at day 0.

TABLE 7

| Protein purity of samples determined by reduced CE-SDS (%) | | | |
| --- | --- | --- | --- |
| Sample | Time | | |
| name | Day 0 | Week 1 | Week 2 | Month 1 |
| pH 5.0 | 98.5 | 98.2 | 97.8 | 98.1 |
| pH 5.5 | 98.5 | 98.2 | 97.8 | 97.8 |
| pH 6.0 | 98.2 | 98.1 | 97.8 | 97.6 |
| pH 6.5 | 98.3 | 97.8 | 97.1 | 96.9 |

(5) Charge Variants

Figure 6:
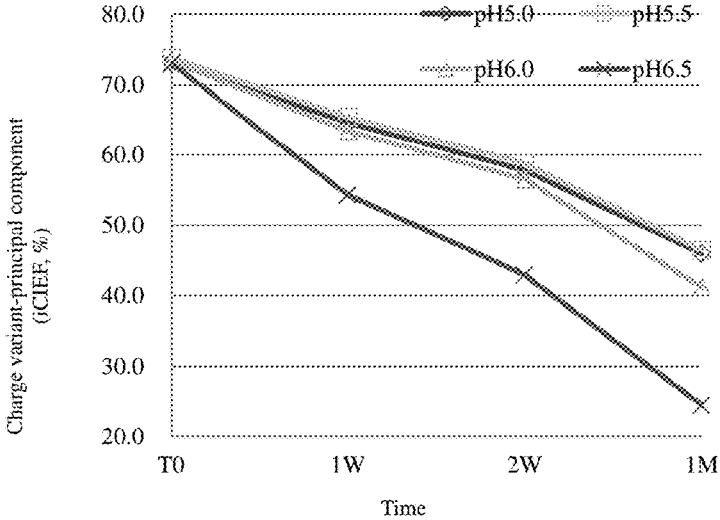
FIG. 6 shows the trend of change in charge variant-principal component of the samples of the anti-PD-1/HER2 bispecific antibody formulation at pH 5.0, 5.5, 6.0 and 6.5 after storage at 40±2° C. for different time periods, as determined by iCIEF. On the abscissa, T0 represents day 0, 1W represents 1 week, 2W represents 2 weeks, and 1M represents 1 month.

After storage at 40±2° C. for different time periods, the charge variants of the samples at pH 5.0, 5.5, 6.0 and 6.5 were determined by iCIEF. The results are shown in Table 8, and the trend of change is shown in FIG. 6. The results show that the principal component and the acidic and basic components of the samples at each pH did not significantly change after examination at 40±2° C. for 1 month. The higher the pH, the faster the principal component of the sample decreased and the faster the acidic component increased.

TABLE 8

| Charge variants of samples determined by iCIEF (%) | | | | | |
| --- | --- | --- | --- | --- | --- |
| | | Time | | | |
| Sample name | | Day 0 | Week 1 | Week 2 | Month 1 |
| pH 5.0 | Acidic component | 24.7 | 28.1 | 33.0 | 44.1 |
| | Principal component | 73.2 | 64.6 | 57.8 | 46.0 |
| | Basic component | 2.1 | 7.3 | 9.2 | 9.9 |
| pH 5.5 | Acidic component | 24.4 | 29.5 | 34.8 | 46.9 |
| | Principal component | 73.8 | 65.4 | 58.8 | 46.5 |
| | Basic component | 1.9 | 5.0 | 6.4 | 6.6 |
| pH 6.0 | Acidic component | 24.5 | 33.0 | 39.6 | 54.9 |
| | Principal component | 73.4 | 63.4 | 56.5 | 41.2 |
| | Basic component | 2.1 | 3.6 | 4.0 | 4.0 |

TABLE 8-continued

| Charge variants of samples determined by iCIEF (%) | | | | |
|---|---|---|---|---|
| | | Time | | |
| Sample name | | Day 0 | Week 1 | Week 2 | Month 1 |

| | | Day 0 | Week 1 | Week 2 | Month 1 |
|---|---|---|---|---|---|
| pH 6.5 | Acidic component | 25.0 | 42.9 | 54.0 | 72.9 |
| | Principal component | 73.0 | 54.3 | 42.9 | 24.5 |
| | Basic component | 2.0 | 2.8 | 3.1 | 2.6 |

(6) Relative Binding Activity

After storage at 40±2° C. for different time periods, the relative binding activity of the samples at pH 5.0, 5.5, 6.0 and 6.5 was determined by direct ELISA. The results are shown in Table 9. The result shows that: after examination at 40±2° C. for 2 weeks, the relative binding activity of each sample for binding to the PD-1 antigen and the HER2 antigen was higher than 70%; the relative binding activity of the anti-HER2 end of the samples at pH 6.0 and 6.5 was remarkably reduced, with both being lower than 70%; after examination at 40±2° C. for 1 month, the relative binding activity of each sample for binding to PD-1 antigen was still higher than 70%, and only in the case of samples at pH 6.0 and pH 6.5, the relative binding activity for binding to HER2 antigen was lower than 70% but still higher than 50%.

TABLE 9

| Relative binding activity of samples determined by direct ELISA (%) | | | | | |
|---|---|---|---|---|---|
| | | | Time | | |
| Sample name | | Day 0 | Week 1 | Week 2 | Month 1 |
| pH 5.0 | Anti PD-1 end | 108 | N/A | 106 | 92 |
| | Anti-HER2 end | 95 | N/A | 87 | 85 |
| pH 5.5 | Anti PD-1 end | 112 | N/A | 102 | 93 |
| | Anti-HER2 end | 98 | N/A | 85 | 81 |
| pH 6.0 | Anti PD-1 end | 108 | N/A | 95 | 94 |
| | Anti-HER2 end | 109 | N/A | 83 | 63 |
| pH 6.5 | Anti PD-1 end | 100 | N/A | 104 | 88 |
| | Anti-HER2 end | 98 | N/A | 86 | 50 |

Note: N/A indicates that the test item is not set.

The test results of the influence of pH on the stability of formulations show that: after the anti-PD-1/HER2 bispecific antibodies at pH 5.0-6.5 were stored at 40±2° C. for 2 weeks, the samples were up to standard in terms of the appearance and visible particles, the protein content did not change significantly, and the relative binding activity for binding to the HER2 antigen and the PD-1 antigen did not changed remarkably, either; in addition, after the anti-PD-1/HER2 bispecific antibodies at pH 5.0-6.5 were stored at 40±2° C. for one month, the samples were up to standard in terms of the appearance and visible particles, the protein content did not change significantly, and the relative binding activity for binding to the PD-1 antigen did not change significantly, either, and the relative binding activity for binding to HER2 antigen of the anti-PD-1/HER2 bispecific antibody was reduced but still higher than 50% only under the conditions of pH 6.0 and 6.5. Thus, in the following examples, pH 5.5 was selected from pH 5.0-6.5 for experiments.

Example 3

Formula Screening Test 3.1. Stabilizer Screening Test

Different stabilizers (sorbitol as a polyol; sucrose and trehalose as saccharides; methionine as an antioxidant; etc.) were examined for their effect on stability of a formulation comprising an anti-PD-1/HER2 bispecific antibody.

3.1.1. Procedures for Stabilizer Screening

A total of 4 formulas were designed, as detailed in Table 10. Buffers of the formulas were prepared as according to Table 10, and the anti-PD-1/HER2 bispecific antibody was exchanged into each formula solution by ultrafiltration. The protein content in each formula solution was adjusted to about 50.0 mg/mL after the exchange, and then polysorbate 80 was added until the final concentration of polysorbate 80 was 0.20 mg/mL. The solutions were filtered and aliquoted into vials, followed by plugging and capping. The stability of the samples was examined at 40° C., 25° C. and 5° C., and the specific scheme is shown in Table 11. The test indexes include appearance, visible particles, protein content, purity (SEC-HPLC and CE-SDS) and charge variants (iCIEF).

TABLE 10

| Information about formulas selected for stabilizer screening test | | |
|---|---|---|
| No. | Information about formula | Information about formula in mg/mL after conversion |
| Formula 1 | 20 mM histidine, 5% sorbitol, 0.02% polysorbate 80, pH 5.5 | 3.10 mg/mL histidine, 50.00 mg/ml sorbitol, 0.20 mg/mL polysorbate 80, pH 5.5 |
| Formula 2 | 20 mM histidine, 8% sucrose, 0.02% polysorbate 80, pH 5.5 | 3.10 mg/mL histidine, 80.00 mg/mL sucrose, 0.20 mg/mL polysorbate 80, pH 5.5 |
| Formula 3 | 20 mM histidine, 8% trehalose, 0.02% polysorbate 80, pH 5.5 | 3.10 mg/mL histidine, 80.00 mg/mL trehalose, 0.20 mg/mL polysorbate 80, pH 5.5 |
| Formula 4 | 20 mM histidine, 8% sucrose, 10 mM methionine, 0.02% polysorbate 80, pH 5.5 | 3.10 mg/mL histidine, 80.00 mg/mL sucrose, 1.49 mg/mL methionine, 0.20 mg/mL polysorbate 80, pH 5.5 |

Note:
the % in the table refers to % w/v; the same applies hereinafter.

TABLE 11

| | Stability examination scheme | |
|---|---|---|
| Name of experiment | Experimental conditions and sampling plan | Test items |
| Forced experiment | Stored at 40° C. for 1 month, sampling at day 0, week 1, week 2 and week 4 | Appearance, visible particles, protein content, purity |
| Accelerated experiment | Stored at 25 ± 2° C. for 2 months, sampling at day 0, month 1 and month 2 | (SEC-HPLC and CE-SDS) and charge variants (iCIEF) |
| Long term experiment | Stored at 5 ± 3° C. for 3 months, sampling at day 0 and month 3 | |

3.1.2. Criteria for Determination

See Table 2 in Example 2 for specific criteria for determination.

3.1.3. Stabilizer Screening Test (1) Appearance and Visible Particles

Observation was carried out for 1 month at 40° C., for 2 months at 25±2° C. and for 3 months at 5±3° C., and the results show that all formula samples were up to standard in terms of appearance and visible particles.

(2) Protein Content

Observation was carried out for 1 month at 40° C., for 2 months at 25±2° C. and for 3 months at 5±3° C., and the results of the protein content of all formula samples are shown in Table 12. The results show that the protein content of the four formulas did not change under three different temperature conditions of 40° C., 25±2° C. and 5±3° C.

TABLE 12

| Protein content results in stabilizer screening test (UV method, mg/mL) | | | | | | |
|---|---|---|---|---|---|---|
| | | 40° C. | | | 25 ± 2° C. | 5 ± 3° C. |
| Name of formula | Day 0 | Week 1 | Week 2 | Week 4 | Month 1 | Month 2 | Month 3 |
| Formula 1 | 50.7 | 50.4 | 50.7 | 48.9 | 49.3 | 48.9 | 50.7 |
| Formula 2 | 50.6 | 50.3 | 50.9 | 50.2 | 49.5 | 49.3 | 51.3 |
| Formula 3 | 50.8 | 50.6 | 51.0 | 49.9 | 50.1 | 49.5 | 51.0 |
| Formula 4 | 51.4 | 51.1 | 51.3 | 50.5 | 51.1 | 50.9 | 51.9 |

(3) Purity

Purity (SEC-HPLC): the results are shown in Table 13. The result shows that: the purity of all formula samples did not change significantly after examination at 40° C. for 4 weeks; the purity of all formula samples did not change significantly after examination at 25±2° C. for 2 months; the purity of all formula samples did not change significantly, either, after examination at 5±3° C. for 3 months.

TABLE 13

| Purity results in stabilizer screening test (SEC-HPLC, %) | | | | | | |
|---|---|---|---|---|---|---|
| | | 40° C. | | | 25 ± 2° C. | 5 ± 3° C. |
| Name of formula | Day 0 | Week 1 | Week 2 | Week 4 | Month 1 | Month 2 | Month 3 |
| Formula 1 | 99.0 | 99.0 | 98.7 | 98.3 | 99.0 | 98.9 | 99.0 |
| Formula 2 | 99.0 | 99.1 | 98.9 | 98.4 | 99.2 | 99.0 | 99.1 |
| Formula 3 | 99.0 | 99.0 | 98.8 | 98.2 | 99.1 | 98.9 | 99.0 |
| Formula 4 | 99.1 | 99.2 | 99.0 | 98.7 | 99.3 | 99.1 | 99.1 |

Purity (non-reduced CE-SDS): the results are shown in Table 14. The result shows that: the purity of all formula samples did not change significantly after examination at 40° C. for 4 weeks; the purity of all formula samples did not change significantly after examination at 25±2° C. for 2 months; the purity of all formula samples did not change significantly, either, after examination at 5±3° C. for 3 months.

TABLE 14

| | | 40° C. | | | 25 ± 2° C. | | 5 ± 3° C. |
|---|---|---|---|---|---|---|---|
| Name of formula | Day 0 | Week 1 | Week 2 | Week 4 | Month 1 | Month 2 | Month 3 |
| Formula 1 | 97.8 | 97.2 | 96.4 | 96.0 | 97.5 | 97.4 | 98.2 |
| Formula 2 | 97.8 | 97.2 | 96.2 | 95.7 | 97.5 | 97.3 | 98.1 |
| Formula 3 | 97.8 | 97.3 | 96.2 | 95.9 | 97.6 | 97.4 | 98.2 |
| Formula 4 | 97.9 | 97.1 | 96.4 | 96.0 | 97.6 | 97.4 | 98.3 |

Purity results in stabilizer screening test (non-reduced CE-SDS, %)

Purity (reduced CE-SDS): the results are shown in Table 15. The result shows that: the purity of all formula samples did not change significantly after examination at 40° C. for 4 weeks; the purity of all formula samples did not change significantly after examination at 25±2° C. for 2 months; the purity of all formula samples did not change significantly, either, after examination at 5±3° C. for 3 months.

TABLE 15

| | | 40° C. | | | 25 ± 2° C. | | 5 ± 3° C. |
|---|---|---|---|---|---|---|---|
| Name of formula | Day 0 | Week 1 | Week 2 | Week 4 | Month 1 | Month 2 | Month 3 |
| Formula 1 | 98.7 | 98.5 | 98.0 | 96.7 | 98.4 | 98.1 | 98.7 |
| Formula 2 | 98.7 | 98.5 | 98.0 | 97.0 | 98.3 | 98.2 | 98.7 |
| Formula 3 | 98.8 | 98.6 | 98.0 | 96.8 | 98.2 | 98.1 | 98.8 |
| Formula 4 | 98.8 | 98.7 | 98.1 | 97.0 | 98.2 | 98.2 | 98.7 |

Purity results in stabilizer screening test (reduced CE-SDS, %)

(4) Charge Variants (iCIEF)

Figure 7:
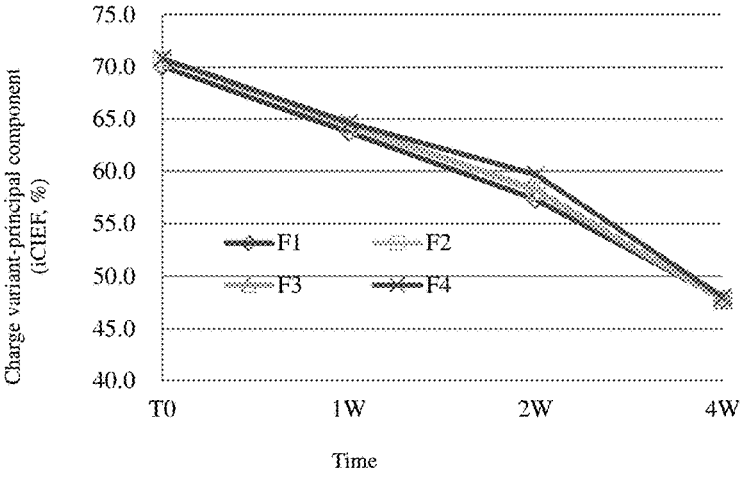
FIG. 7 shows the change in charge variant-principal component over time of the anti-PD-1/HER2 bispecific antibody formulations comprising different stabilizers (formulas 1-4) after storage at 40° C. for 0 days, 1 week, 2 weeks and 4 weeks, as determined by iCIEF. On the abscissa, T0 represents day 0, 1W represents 1 week, 2W represents 2 weeks, 4W represents 4 weeks, F1 represents formula 1, F2 represents formula 2, F3 represents formula 3, and F4 represents formula 4.
Figure 8:
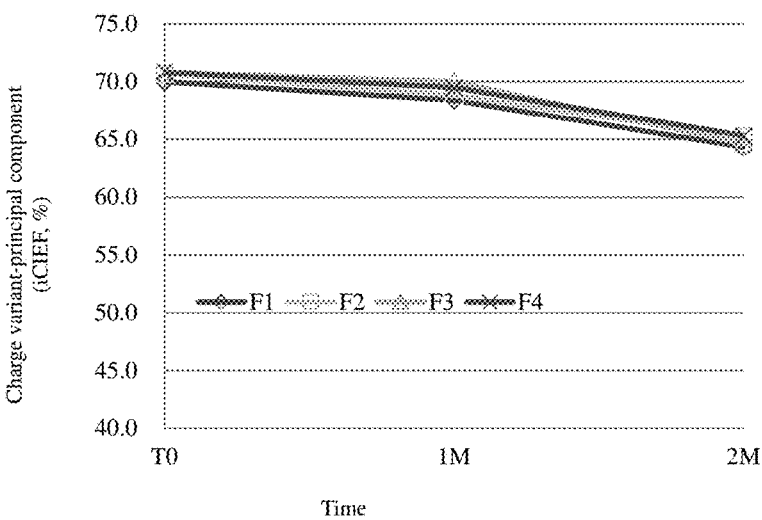
FIG. 8 shows the change in charge variant-principal component over time of the anti-PD-1/HER2 bispecific antibody formulations comprising different stabilizers (formulas 1-4) after storage at 25±2° C. for 0 days, 1 week, 2 weeks and 4 weeks, as determined by iCIEF. On the abscissa, T0 represents day 0, 1M represents 1 month, 2M represents 2 months, F1 represents formula 1, F2 represents formula 2, F3 represents formula 3, and F4 represents formula 4.

Charge variants (iCIEF): the results are shown in Table 16. The trends of change in the charge variant-principal component of each formula at 40° C. and 25±2° C. are shown in FIG. 7 and FIG. 8, respectively.

The results show that: after examination at 40° C. for 4 weeks, the principal component and the acidic and basic components in the charge variants of all formula samples changed significantly; the principal component decreased, and the acidic component increased; the trends of change of the samples were basically the same, and there was no significant difference between formulas 1-4. After acceleration at 25±2° C. for 2 months, the principal component and the acidic and basic components in the charge variants of all formula samples changed significantly; the principal component decreased, and the acidic component increased; the trends of change of the formulas were basically the same, and there was no significant difference between formulas 1-4. After examination at 5±3° C. for 3 months, the principal component and the acidic and basic components in the charge variants of all formula samples did not change significantly.

TABLE 16

| | | | 40° C. | | | 25 ± 2° C. | | 5 ± 3° C. |
|---|---|---|---|---|---|---|---|---|
| Name of formula | | Day 0 | Week 1 | Week 2 | Week 4 | Month 1 | Month 2 | Month 3 |
| Formula 1 | Acidic component | 27.4 | 30.1 | 36.1 | 45.7 | 27.6 | 31.8 | 28.1 |
| | Principal component | 70.0 | 63.7 | 57.3 | 47.8 | 68.4 | 64.3 | 69.2 |
| | Basic component | 2.6 | 6.2 | 6.5 | 6.5 | 4.1 | 3.9 | 2.7 |
| Formula 2 | Acidic component | 26.8 | 29.4 | 35.8 | 46.3 | 27.0 | 30.9 | 27.6 |
| | Principal component | 70.7 | 64.3 | 58.1 | 47.1 | 68.8 | 65.2 | 69.7 |
| | Basic component | 2.5 | 6.3 | 6.1 | 6.7 | 4.2 | 4.0 | 2.8 |
| Formula 3 | Acidic component | 26.7 | 29.9 | 35.4 | 45.8 | 26.2 | 31.4 | 28.1 |
| | Principal component | 70.8 | 64.4 | 58.3 | 47.7 | 70.0 | 64.6 | 69.0 |
| | Basic component | 2.5 | 5.8 | 6.3 | 6.5 | 3.9 | 4.1 | 2.9 |

Charge variant results in stabilizer screening test (iCIEF, %)

TABLE 16-continued

| Charge variant results in stabilizer screening test (iCIEF, %) | | | | | | | |
| | | | 40° C. | | | 25 ± 2° C. | | 5 ± 3° C. |
| Name of formula | Day 0 | Week 1 | Week 2 | Week 4 | Month 1 | Month 2 | Month 3 |
| Formula 4 Acidic component | 26.7 | 29.3 | 33.8 | 45.3 | 26.2 | 30.5 | 27.4 |
| Principal component | 70.8 | 64.6 | 59.7 | 48.0 | 69.5 | 65.3 | 69.8 |
| Basic component | 2.5 | 6.1 | 6.5 | 6.7 | 4.3 | 4.2 | 2.9 |

The results of the formula determination experiment show that formulas 1-4 are relatively consistent in trend of change, and there's no significant difference between them. In terms of the simplicity of formula, there was no significant difference in the protection of protein for formula 1, formula 2 and formula 3 with a single stabilizer, and in view of the development of a lyophilized formulation later, formula 2 was selected. For safety in the later production, in the buffer system of formula 2, concentrated hydrochloric acid was replaced with histidine and histidine hydrochloride in adjusting the pH. To ensure the stability of the adjusted formulation formula, the following experiment was further performed.

Example 4

Formula Confirmation Experiment

4.1. Formula Design and Experimental Scheme

Formula 5 was designed, and the details of formula 5 are shown in Table 17.

TABLE 17

| Information about formula | |
| No. | Information about formula |
| Formula 5 | 42.0 mg/mL recombinant fully human anti-programmed death receptor 1 (PD-1) and humanized anti-human epidermal growth factor receptor 2 (HER2) bispecific antibody, 0.85 mg/mL histidine, 3.17 mg/mL histidine hydrochloride, 80.00 mg/mL sucrose, 0.2 mg/mL polysorbate 80, pH 5.5 |

The scheme of the formula confirmation experiment is shown in Table 18.

TABLE 18

| Scheme of formula confirmation experiment | | |
| Name of experiment | Experimental conditions and sampling plan | Test items |
| Forced experiment | Stored at 40° C. for 1 month, sampling at day 0, week 2 and week 4 | Appearance, visible particles, protein content, purity (SEC-HPLC and CE-SDS), charge variants (iCIEF) and relative binding activity (direct ELISA) |

4.2. Experimental Results

The results of the 40° C. forced experiment are shown in Table 19. After storage at 40° C. for 4 weeks, the sample was up to standard in terms of the appearance, visible particles and biological activity, the protein content and the purity (SEC-HPLC and CE-SDS) did not change significantly, and only the charge variant-principal component (iCIEF) decreased by 16.0%, the acidic component increased by 14.0%, and the basic component increased by 2.0%.

TABLE 19

| Results of stability experiment | | | | |
| | | | Time | |
| | Sample name | Day 0 | Week 2 | Week 4 |
| Formula 5 | Protein content (mg/mL) | 39.4 | 42.8 | 42.5 |
| | Purity (SEC-HPLC, %) | 97.0 | 97.0 | 96.6 |
| | Purity (non-reduced CE-SDS, %) | 95.8 | 95.8 | 93.9 |
| | Charge variants (iCIEF, %) Acidic component | 31.0 | 36.2 | 45.0 |
| | Principal component | 65.8 | 58.6 | 49.8 |
| | Basic component | 3.2 | 5.3 | 5.2 |
| | Anti-PD-1 end (direct ELISA, %) | 92 | N/A | 84 |
| | Anti-HER2 end (direct ELISA, %) | 91 | N/A | 78 |

The results show that 42.0 mg/mL recombinant fully human anti-programmed death receptor 1 (PD-1) and humanized anti-human epidermal growth factor receptor 2 (HER2) bispecific antibody disclosed herein has a trend of change in formula 5 (0.85 mg/mL histidine, 3.17 mg/mL histidine hydrochloride, 80.00 mg/mL sucrose, 0.2 mg/mL polysorbate 80, pH 5.5) that is relatively consistent with that in formula 2 in Example 3.

Thus, the most preferred formulation scheme is determined to be: about 42.0 mg/mL recombinant fully human anti-programmed death receptor 1 (PD-1) and humanized anti-human epidermal growth factor receptor 2 (HER2) bispecific antibody, 0.85 mg/mL histidine, 3.17 mg/mL histidine hydrochloride, 80.00 mg/mL sucrose, 0.2 mg/mL polysorbate 80, pH 5.5.

The exemplary embodiments of the present invention have been described above. It should be understood by those skilled in the art that these contents are merely exemplary, and various other replacements, adaptations and modifications can be made within the scope of the present invention. Accordingly, the present invention is not limited to the specific embodiments listed herein.

The invention claimed is:

1. A liquid antibody formulation, comprising:

(i) an anti-PD-1/HER2 bispecific antibody protein;

(ii) a buffer;

(iii) a stabilizer, and (iv) a surfactant, wherein the anti-PD-1/HER2 bispecific antibody protein comprises a first half antibody and a second half antibody, wherein the first half antibody comprises a first VH/VL unit specifically binding to PD-1, and the second half antibody comprises a second VH/VL unit specifically binding to HER2, wherein the first VH/VL unit comprises all heavy chain CDRs and light chain CDRs contained in paired heavy chain variable region/light chain variable region sequences set forth in SEQ ID NO: 12/SEQ ID NO: 10, and the second VH/VL unit comprises all heavy chain CDRs and light chain CDRs contained in paired heavy chain variable region/light chain variable region sequences set forth in SEQ ID NO: 6/SEQ ID NO: 2; and wherein the first half antibody comprises heavy chain sequences set forth in SEQ ID NO: 12 and SEQ ID NO: 14 in N to C direction and comprises light chain sequences set forth in SEQ ID NO: 10 and SEQ ID NO: 4 in N to C direction, and the second half antibody comprises heavy chain sequences set forth in SEQ ID NO: 6 and SEQ ID NO: 8 in N to C direction and comprises light chain sequences set forth in SEQ ID NO: 2 and SEQ ID NO: 4 in N to C direction; and wherein the liquid antibody formulation is selected from a group consisting of:

(A) (i) about 42 mg/mL anti-PD-1/HER2 bispecific antibody protein;

(ii) about 0.85 mg/mL histidine and about 3.17 mg/mL histidine hydrochloride;

(iii) about 80 mg/mL sucrose; and (iv) about 0.2 mg/mL polysorbate 80;

(B) (i) about 50 mg/mL anti-PD-1/HER2 bispecific antibody protein;

(ii) about 20 mM histidine;

(iii) about 50 mg/mL sorbitol; and (iv) about 0.2 mg/mL polysorbate 80;

(C) (i) about 50 mg/mL anti-PD-1/HER2 bispecific antibody protein;

(ii) about 20 mM histidine;

(iii) about 80 mg/mL sucrose; and (iv) about 0.2 mg/mL polysorbate 80;

(D) (i) about 50 mg/mL anti-PD-1/HER2 bispecific antibody protein;

(ii) about 20 mM histidine;

(iii) about 80 mg/mL trehalose; and (iv) about 0.2 mg/mL polysorbate 80; and (E) (i) about 50 mg/mL anti-PD-1/HER2 bispecific antibody protein;
 (ii) about 20 mM histidine;
 (iii) about 80 mg/mL sucrose and about 1.49 mg/mL methionine; and
 (iv) about 0.2 mg/mL polysorbate 80; and
 wherein the pH of the liquid antibody formulation is about 5.0-6.0.

2. The liquid antibody formulation according to claim 1, wherein the anti-PD-1/HER2 bispecific antibody is recombinantly expressed in HEK293 cells or HEK293T, HEK293F or HEK293E cells obtained by modification based on HEK293 cells and in CHO cells or CHO-S, CHO-dhfr⁻, CHO/DG44 or ExpiCHO cells obtained by modification based on CHO cells.

3. The liquid antibody formulation according to claim 1, wherein the liquid formulation is an injection formulation, or an infusion formulation.

4. The liquid antibody formulation according to claim 3, wherein the liquid formulation is an injection formulation for subcutaneous or intravenous injection, or an infusion formulation for intravenous infusion.

5. The liquid antibody formulation according to claim 1, wherein the formulation is stable after storage at 2-8° C. for at least 24 months, at room temperature for at least 3 months, or at 40±2° C. for 1 month, and the formulation has one or more of the following characteristics:
 (i) a purity greater than 90%, as measured by SEC-HPLC;
 (ii) a purity greater than 90%, as measured by reduced or non-reduced CE-SDS;
 (iii) total change ≤50% in components (principal component, acidic component and basic component) of the anti-PD-1/HER2 bispecific antibody in the formulation, relative to an initial value on day 0 of storage, as measured by iCIEF; and
 (iv) relative binding activity of the anti-PD-1/HER2 bispecific antibody in the formulation of 70-130%, relative to an initial value on day 0 of storage, as measured by ELISA.

6. A delivery device, comprising the liquid antibody formulation according to claim 1.

7. The delivery device according to claim 6, wherein the delivery device is a pre-filled syringe.

\* \* \* \* \*